United States Patent
Cossler et al.

(10) Patent No.: US 11,587,653 B2
(45) Date of Patent: *Feb. 21, 2023

(54) GRAPHICAL USER INTERFACE FOR TRACKING AND DISPLAYING PATIENT INFORMATION OVER THE COURSE OF CARE

(71) Applicant: University Hospitals of Cleveland, Cleveland, OH (US)

(72) Inventors: Nancy Cossler, Solon, OH (US); Jeffrey Beers, Olmsted Falls, OH (US)

(73) Assignee: UNIVERSITY HOSPITALS OF CLEVELAND, Cleveland, OH (US)

( * ) Notice: Subject to any disclaimer, the term of this patent is extended or adjusted under 35 U.S.C. 154(b) by 30 days.

This patent is subject to a terminal disclaimer.

(21) Appl. No.: 16/707,606

(22) Filed: Dec. 9, 2019

(65) Prior Publication Data

US 2020/0111551 A1  Apr. 9, 2020

Related U.S. Application Data

(63) Continuation of application No. 14/304,593, filed on Jun. 13, 2014, now Pat. No. 10,529,445.

(51) Int. Cl.
*G16H 10/60* (2018.01)
*G16H 15/00* (2018.01)

(52) U.S. Cl.
CPC ............. *G16H 10/60* (2018.01); *G16H 15/00* (2018.01)

(58) Field of Classification Search
CPC ........ G16H 10/60; G16H 50/20; G16H 50/30; G16H 50/70
(Continued)

(56) References Cited

U.S. PATENT DOCUMENTS 5,357,427 A  10/1994 Langen et al.
6,322,502 B1  11/2001 Schoenberg et al.
(Continued)

FOREIGN PATENT DOCUMENTS

KR  10-2007-011716 A  12/2007
WO  98/29790 A2  7/1998
(Continued)

OTHER PUBLICATIONS

Li, Zheng; Non-linear adaptive Bayesian filtering for brain machine interfaces; Duke University. ProQuest Dissertations Publishing, 2010. 3398437 (Year: 2010).*
(Continued)

*Primary Examiner* — Hiep V Nguyen

(74) *Attorney, Agent, or Firm* — Amin, Turocy & Watson, LLP

(57) ABSTRACT

A system for generating an interface that tracks information over the course of patient care is provided. The system includes an interface component configured to generate an interface that facilitates tracking a course of care of a patient, wherein the interface comprises a plurality of input compartments defined by a first axis comprising columns corresponding to sequential points in time over the course of the care and a second axis comprising rows respectively corresponding to patient care events or patient conditions associated with the course of the care. The system further includes a reception component configured to receive input regarding a patient care event or condition that occurred over the course of the care, and a logging component configured to fill one or more input compartments respectively corresponding to a point or period of time associated with occurrence of the patient care event or patient condition.

21 Claims, 14 Drawing Sheets

(6 of 14 Drawing Sheet(s) Filed in Color)

(58) Field of Classification Search
USPC .......................................................... 705/3
See application file for complete search history.

(56) References Cited

U.S. PATENT DOCUMENTS

| | | | |
|---|---|---|---|
| 7,374,535 B2 | 5/2008 | Schoenberg et al. | |
| 7,693,727 B2 * | 4/2010 | Moore ................... | G16H 50/20 |
| | | | 705/2 |
| 7,778,851 B2 | 8/2010 | Schoenberg et al. | |
| 7,831,450 B2 | 11/2010 | Schoenberg et al. | |
| 7,899,683 B2 | 3/2011 | Schoenberg et al. | |
| 8,027,846 B2 | 9/2011 | Schoenberg et al. | |
| 8,376,943 B2 | 2/2013 | Kovach et al. | |
| 2002/0177758 A1 | 11/2002 | Schoenberg et al. | |
| 2002/0177759 A1 | 11/2002 | Schoenberg et al. | |
| 2003/0036687 A1 | 2/2003 | Schoenberg et al. | |
| 2005/0125256 A1 | 6/2005 | Schoenberg et al. | |
| 2005/0228243 A1 | 10/2005 | Bardy | |
| 2006/0265249 A1 | 11/2006 | Follis et al. | |
| 2007/0022075 A1 * | 1/2007 | Horvitz ................. | G06N 7/005 |
| | | | 706/52 |
| 2008/0208618 A1 | 8/2008 | Schoenberg et al. | |
| 2009/0082640 A1 | 3/2009 | Kovach et al. | |
| 2009/0147011 A1 | 6/2009 | Buck et al. | |
| 2009/0259487 A1 * | 10/2009 | Rao ........................ | G16H 70/60 |
| | | | 705/2 |
| 2010/0250196 A1 | 9/2010 | Lawler et al. | |
| 2011/0004489 A1 | 1/2011 | Schoenberg et al. | |
| 2012/0089553 A1 | 4/2012 | Mollicone et al. | |
| 2012/0303388 A1 | 11/2012 | Vishnubhatla et al. | |
| 2013/0151285 A1 | 6/2013 | McLaren et al. | |
| 2013/0152005 A1 | 6/2013 | McLaren et al. | |
| 2013/0191165 A1 * | 7/2013 | MacDonald ........... | G16H 10/60 |
| | | | 705/3 |
| 2013/0218053 A1 | 8/2013 | Kaiser et al. | |
| 2014/0028464 A1 | 1/2014 | Garibaldi | |

FOREIGN PATENT DOCUMENTS

| | | | | |
|---|---|---|---|---|
| WO | 2013/173715 A1 | 11/2013 | | |
| WO | WO-2013173715 A1 * | 11/2013 | ............. | G06Q 40/00 |

OTHER PUBLICATIONS

U.S. Appl. No. 15/900,009, filed Feb. 20, 2018.
Non-Final Office Action received for U.S. Appl. No. 15/900,009 dated Nov. 3, 2020, 20 pages.
Final Office Action received for U.S. Appl. No. 15/900,009 dated May 28, 2020, 24 pages.
International Search Report and Written Opinion for PCT Application Serial No. PCT/US2015/035359 dated Sep. 7, 2015, 12 pages.
Non-Final Office Action received for U.S. Appl. No. 14/304,593 dated Sep. 19, 2016, 18 pages.
Final Office Action received for U.S. Appl. No. 14/304,593 dated Feb. 1, 2017, 23 pages.
Office Action for U.S. Appl. No. 14/304,593 dated Jul. 7, 2017, 24 pages.
Final Office Action for U.S. Appl. No. 14/304,593 dated Apr. 17, 2018, 26 pages.
Non-Final Office Action for U.S. Appl. No. 14/304,593 dated Oct. 25, 2018, 20 pages.
Final Office Action received for U.S. Appl. No. 14/304,593 dated Mar. 20, 2019, 24 pages.
Final Office Action received for U.S. Appl. No. 15/900,009 dated Oct. 28, 2019, 34 pages.
Final Office Action received for U.S. Appl. No. 15/900,009 dated Jun. 8, 2021, 28 pages.
Final Office Action received for U.S. Appl. No. 16/707,606 dated Sep. 24, 2021, 21 pages.
Notice of Allowance received for U.S. Appl. No. 15/900,009 dated Apr. 28, 2022, 73 pages.
Phansalkar S., "Advanced methods for detection of adverse drug events in clinical notes", The University of Utah, ProQuest Dissertations Publishing, 2007, 135 pages.

* cited by examiner

Patient Name": 38 yr old. 37 wks gestation, G3P2 Plan: TOLAC

| hours | 0 | 4 | 8 | 12 | 16 | 20 | 24 | 26 |
|---|---|---|---|---|---|---|---|---|
| Admit | | | | | | | Admit 24 hr | |
| ROM | | | | | | | ROM 16 hr | |
| Cytotec | | | | | | Cytotec 8 hr | | |
| Pitocin | | | | | | Pitocin 4 hr | | |
| Stage | Stage 1 | | | | | | Stage II | |
| Category | | | | | | Category I | Category II | |
| Dilation | 2cm | | 4cm | 4cm 8hr | 6cm 4hr | 9cm | Complete | |
| BP | 138/85 | | | 150/95 | 160/100 | | 145/85 | |
| Mag | | | | | | | Mag 8hrs | |
| HR | 90 | | 85 | | 90 | | 92 | |
| Temp | 36.9 | | 37.1 | | 37.2 | | 36.8 | |
| Decel | | | | | | | | |
| Acceleration | | | 30 secs | | | | | |

FIG. 1

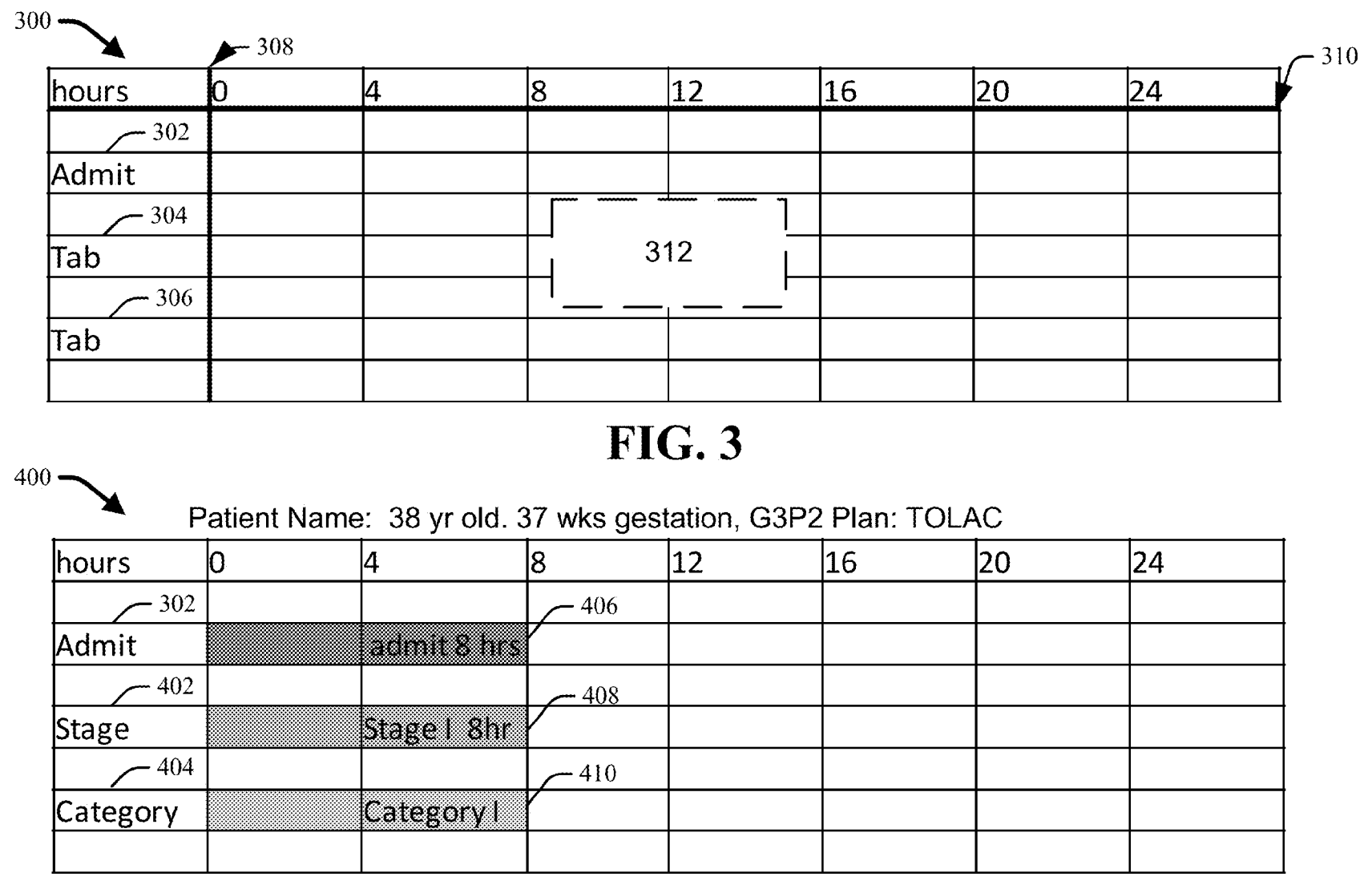

| hours | 0 | 4 | 8 | 12 | 16 | 20 | 24 | |
|---|---|---|---|---|---|---|---|---|
| Admit — 304 | | | | | | | | |
| Tab — 306 | | | | 312 | | | | |
| Tab | | | | | | | | |

FIG. 3

Patient Name: 38 yr old. 37 wks gestation, G3P2 Plan: TOLAC

| hours | 0 | 4 | 8 | 12 | 16 | 20 | 24 | |
|---|---|---|---|---|---|---|---|---|
| Admit — 402 | | | admit 8 hrs | | | | | |
| Stage — 404 | | | Stage I 8hr | | | | | |
| Category | | | Category I | | | | | |

FIG. 4

| Labor Clinical Decision Data Display | | | | | | | | | | | |
|---|---|---|---|---|---|---|---|---|---|---|---|
| Date | 1/7/2014 | | | | | | | | | | |
| Clock | 1500 | 1600 | 1700 | 1800 | 1900 | 2000 | 2100 | 2200 | 2300 | 2400 | |
| Number of hours | 1 | 2 | 3 | 4 | 5 | 6 | 7 | 8 | 9 | 10 | |
| Decision to Induce | | | | | | | | | 828 | | |
| Active Phase | | | | | | | | | 830 | | |
| Rupture of Membranes | | | | | | | | | | 832 | |
| Induction Pharmaceutical | Cytotec #1 | | 834 | | | | | Cytotec #2 | | | |
| Oxytocin | | | | | | | | | 838 | | |
| Dilatation | | | | | | | | | 840 | | |
| Fetal Heart Baseline Rate | Baseline FHR 156 | | | | | 836 | | | | 842 | |
| Deceleration >2 minutes | | | | | | | | | | | |
| Maternal Temperature >= 38.0 C | | | | | | | | | | | |
| Maternal Hypertension > 160/110 | | | | | | | | | | | |
| Other | | | | | | | | | | | |

FIG. 8A

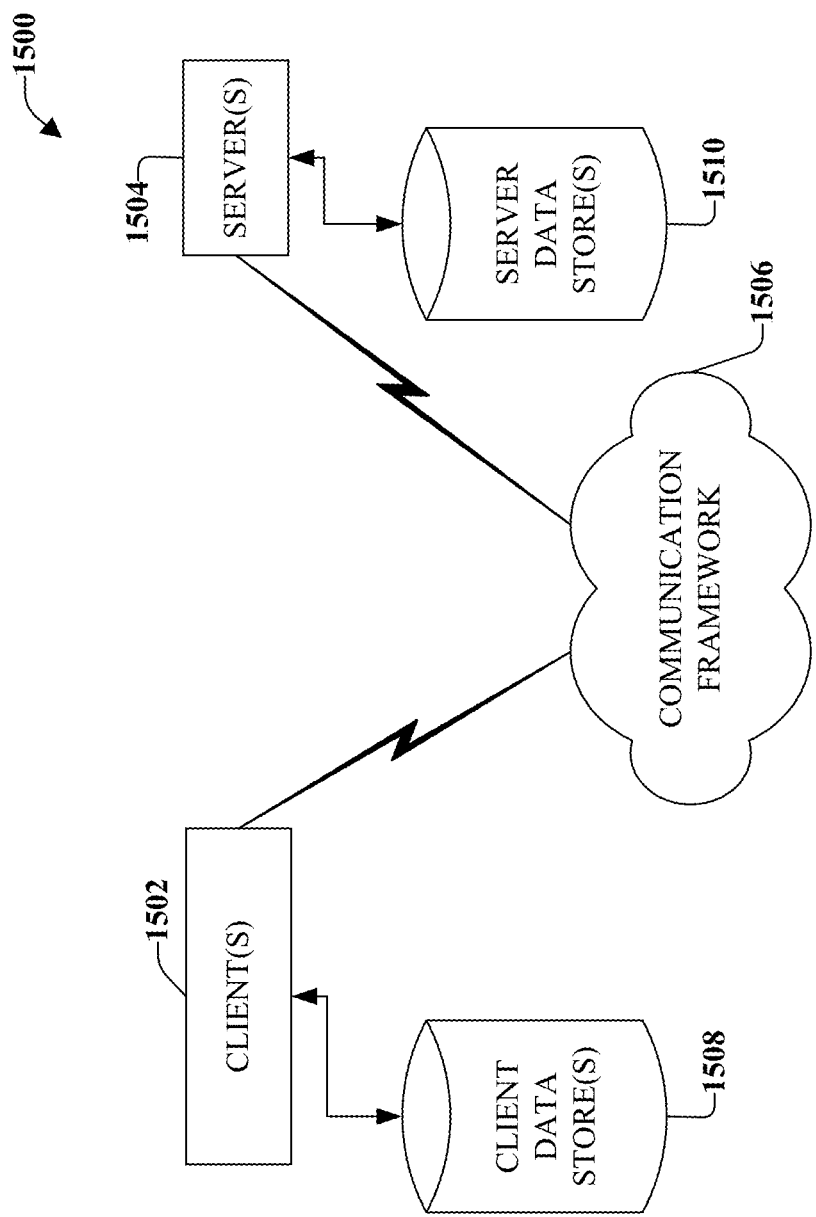

GRAPHICAL USER INTERFACE FOR TRACKING AND DISPLAYING PATIENT INFORMATION OVER THE COURSE OF CARE

CROSS-REFERENCE TO RELATED APPLICATIONS

This application is continuation of and claims priority to U.S. patent application Ser. No. 14/304,593 filed on Jun. 13, 2014, entitled "GRAPHICAL USER INTERFACE FOR TRACKING AND DISPLAYING PATIENT INFORMATION OVER THE COURSE OF CARE." The entirety of the aforementioned application is incorporated by reference herein.

TECHNICAL FIELD

This disclosure relates a graphical user interface for tracking and displaying patient information over the course of care.

BACKGROUND

In health care settings, tracking of patients, patient services, medications, and other items or services can provide both better immediate management of patient care and better long-term management as tracking reports are evaluated to determine where problem areas exist. In healthcare delivery systems, patient flow can be critical, both to the individual patient and to the overall patient population. For example, management of a patient in labor involves various key data and decision points over the course of labor that guide the physician, midwife or nurse in their scope of clinical decision making. These key data points are difficult to track for each patient in a clear and concise fashion over the length of labor. Keeping track of up to the moment data as a clinician moves between multiple laboring patients may be difficult.

There is a significant opportunity for improvement in tracking patient conditions and health services over the course of patient care. The various transactions involved with a patient admitted to a hospital related to treatment, diagnosis and recovery are currently unmanaged and poorly integrated and coordinated. The looseness of this process results in errors, omissions, missing information, duplication, re-work, inefficiency, sub-optimal quality, poor service, and high cost to the patient and health care provider.

BRIEF DESCRIPTION OF THE DRAWINGS

This application contains at least one drawing executed in color. Copies of this patent or patent application publication with color drawing(s) will be provided by the Office upon request and payment of the necessary fee.

FIG. 1 illustrates a block diagram of an example user interface facilitates tracking and displaying patient information over the course of care in accordance with various aspects and embodiments described herein;

FIG. 3 illustrates a block diagram of another example user interface facilitates tracking and displaying patient information over the course of care in accordance with various aspects and embodiments described herein;

FIG. 4 illustrates a block diagram of another example user interface facilitates tracking and displaying patient information over the course of care in accordance with various aspects and embodiments described herein;

FIGS. 8A-8B illustrate a block diagram of another example user interface facilitates tracking and displaying patient information over the course of care in accordance with various aspects and embodiments described herein;

FIG. 15 is a schematic block diagram of a sample-computing environment in accordance with various aspects and embodiments.

DETAILED DESCRIPTION

Figure 2:
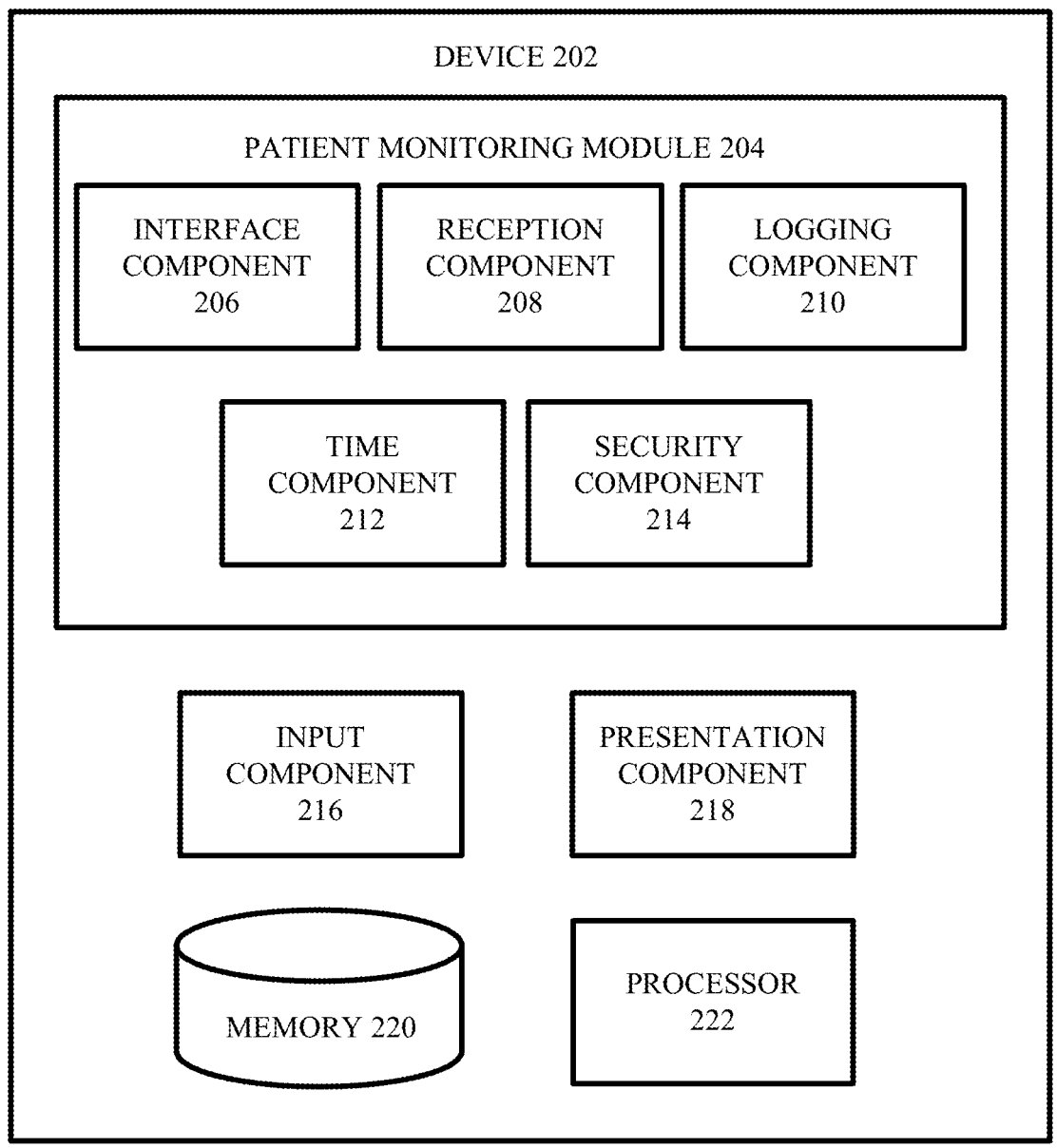
FIG. 2 presents an example system that facilitates tracking and displaying patient information over the course of care in accordance with various aspects and embodiments described herein.

The innovation is described with reference to the drawings, wherein like reference numerals are used to refer to like elements throughout. In the following description, for purposes of explanation, numerous specific details are set forth in order to provide a thorough understanding of this innovation. It may be evident, however, that the innovation can be practiced without these specific details. In other instances, well-known structures and components are shown in block diagram form in order to facilitate describing the innovation.

By way of introduction, the subject matter described in this disclosure relates to systems and methods that enable health care providers to efficiently and effectively manage care of their patients. In an aspect, a system is provided that includes a patient tracking tool that facilitates receiving input regarding patient care events and patient conditions over the course of patient care. The patient tracking tool includes an interface component configured to generate a graphical user interface (GUI) that facilitates tracking a course of patient care. The interface can include a visualization that resembles a chart having a plurality of input compartments defined by a first axis having columns corresponding to sequential points in time over the course of the care and a second axis having rows respectively corresponding to patient care events or patient conditions associated with the course of the care. The patient tracking tool further includes a reception component configured to receive input regarding a patient care event or condition that occurred over the course of the care and a logging component configured to fill one or more input compartments respectively corresponding to a point or period of time associated with occurrence of the patient care event or patient condition, in response to reception of the input.

In an aspect, the patient tracking tool can be provided on a device that is accessible to medical personal involved in the patient care. The device can include a display that presents the interface to the medical personnel and allows the medical personnel to provide the input (e.g., via touch screen or other input device) regarding occurrence of a patient care event or condition. For example, the patient tracking tool can be provided on a device located in a patient's hospital room. The patient tracking tool can generate a graphical user interface that is displayed on the device and charts up to date information regarding conditions of the patient (e.g., heart rate, blood pressure, temperature, etc.) and events (e.g., administration of a drug) associated with care of the patient from the time of admittance to a current point in time. Over the course of care, medical personnel can input the information in real-time for display via the graphical user interface and/or the information can be received in real time from a medical device (e.g., a heart monitor, pulse oximetry device, etc.). As a result, the graphical user interface can depict a complete timeline picture of the various aspects of a course of patient care from the time of admittance to a current point in time.

In an aspect, at the time a patient is admitted or received, the patient's medical history and a plan for the patient care is entered using the patient tracking tool. The patient tracking tool generates a graphical user interface that includes a date and hours timeline that run horizontally (e.g., left to right or an X axis) and a plurality of data fields that extend vertically (e.g., from top to bottom or a Y axis) and below the hours timeline near the left side of the interface. For example, a series of ten to fifteen data fields related to patient conditions and/or patient care events associated with the plan for patient care can be displayed along a vertical axis tangential from the timeline. In an aspect, the data fields can be associated with a drop down input menu that allows a user to select an input option from a plurality of preconfigured input options associated with the data field.

In an aspect, received input data can start a timeline associated with a patient condition or patient care event. Once a timeline is started it will continue to progress across the interface until new data is received indicating a change in the patient condition or patient care event. In another aspect, received input data can identify a particular time point that a key event or condition occurred in the course of care. A timeline or key event can be represented by a color bar running horizontally right to left across the interface. In an aspects, characteristics associated with a timeline or key event can be included in the form of text or a symbol located at the tip of the color bar.

In an exemplary embodiment, the subject patient tracking tool can facilitate tracking patient care during a course of labor. For example, management of a patient in labor may be brief, over a few hours, or may last several days. Clinicians in most hospital based services are limited to 8 or 12 hour "on duty" time frames or "shifts." Accordingly, the care of a mother in labor management often crosses through the care of many clinicians. Depending on the patient care setting, clinicians involved with care can include attending medical doctors (MDs), residents, interns, nurse midwives, registered nurses (RNs), licensed practical nurses (LPNs), patient care assistants and doulas interacting with the laboring patient. Clinicians often cover multiple laboring patients at once and in some cases, information regarding a patient's labor is communicated to a remote physician to make patient care decisions based on the communicated information. Therefore, accurate and effective communication from one clinician to another over the course of a patient's labor and delivery is paramount to a successful labor and delivery.

There are key data and decision points in the course of labor that can affect the outcome of the baby including lifelong cognitive and physical functions. Data points that guide the physician, midwife of nurse in their scope of clinical decision making are difficult to track for each patient in a clear and concise fashion over the length of labor. Keeping track of up to the moment data as a clinician moves between multiple laboring patients may be difficult. The subject patient tracking tool can provide clinicians with comprehensive picture of the key data and decision points during the course of labor management.

Various aspects of the subject patient tracking tool are exemplified in association with tracking patient care over the course of labor. However, it should be appreciated that the subject patient tracking tool is not limited to tracking patients undergoing labor. The subject patient tracking tool can be employed to track patient care events and conditions associated with a patient care scenario that involves caring for the patient over a period of time. For example, the subject patient tracking tool can be employed to manage patient care with respect to treatment of various diseases over a period of time. In another example, the subject patient tracking tool can be employed to manage course of care of patients admitted to the emergency room for various ailments. Still in yet another example, the subject patient tracking tool can assist in managing a course of care for a patient suffering from a heart attack or stroke.

Referring now to the drawings, FIG. 1 depicts an example user interface 100 that facilitates tracking patient care events and patient conditions over the course of labor in accordance with aspects and embodiments described herein. Aspects of the interfaces, apparatuses, systems or processes described in this disclosure can constitute machine-executable components or modules embodied within machine(s), e.g., embodied in one or more computer readable mediums (or media) associated with one or more machines. Such components or modules, when executed by the one or more machines, e.g., computer(s), computing device(s), virtual machine(s), etc. can cause the machine(s) to perform the operations described.

Interface 100 organizes and presents information associated with care of a patient over the course of labor as a function of time. In particular, interface 100 graphically depicts various patient care events and conditions that occurred over the course of labor up until a time of 24 hours after admittance of the patient. Interface 100 includes a plurality of input compartments or cells defined by a first axis 102 and a second axis 130. The first axis 102 corresponds to a timeline and includes a plurality of columns respectively associated with sequential points in time, beginning with a time at which the patient was admitted. For example, the first axis 102 includes a plurality of columns respectively associated with four hour increments of time following admittance of the patient. The second axis 130 includes a plurality of rows respectively associated with a data input fields corresponding to patient care events or conditions. In particular, the second axis 130 includes a plurality of rows that correspond to various patient care events and conditions associated with labor, including admittance 104, rupture of membranes (ROM) 106, provision of cytotec 108, provision of pitocin 110, stages of labor 112 (e.g., associated with the mother and/or the infant), categories of labor 114 (e.g., associated with the mother and/or the infant), dilation 116, blood pressure (BP) 118, magnesium (Mag) or maternal hypertension 120, fetal heart rate (HR) 122, maternal temperature 124, deceleration of fetal HR 126, and acceleration of fetal HR 128.

It should be appreciated that the data fields corresponding to the respective rows of interface 100 are not limited to those described above. In particular, a data field in interface 100 can be adapted to correspond to any possible patient care event or condition associated with a course of labor. For example, one or more of the data fields listed above and depicted in interface 100 can be removed and/or additional data fields can be added. For instance, row 120 corresponding to Mag monitoring could be removed and a new row could be added corresponding to fetal station that facilitates tracking information regarding fetal station. In an aspect, interface 100 can be divided into two sections, one having data input rows corresponding to patient care events and conditions associated with the mother and another corresponding to patient care events and conditions associated with the infant.

Interface 100 graphically depicts various patient care events and conditions that occurred over the course of labor up until a time of 24 hours after admittance of the patient. Information or data included within respective input compartments or cells of interface 100 can be received and entered over the course of care at the time at which a patient event or condition represented by the data occurs. For example, a user can select a cell (e.g., cell 156) corresponding to a time or hour increment (e.g., 12 hours) and data input field (e.g., dilation 116) and enter information for display in the cell indicating occurrence and/or a characteristic of the patient care event or condition represented by the data field at the time or hour increment (e.g., 4 centimeters (cm) for 8 hours (hr)).

In an aspect, information or data included within respective input compartments of interface 100 is entered by a medical caregiver. For example, using a data interfacing tool (e.g., soft keys, touch screen, voice detection, etc.), a user can select an input compartment defined by a row and a column and enter information representative of the patient care event or condition associated with the row at a time represented by the column. The entered information can include a fill color and/or text indicating occurrence of the patient care event or condition and/or identifying a characteristic of the patient care event or condition. In another aspect, information or data included within respective input compartments of interface 100 is entered automatically in response to receipt of the information from a medical device (e.g., a heart rate monitor, a temperature monitor, etc.).

Interface 100 can receive and display various types of data input to indicate occurrence and/or a characteristic of the patient care event or condition. For example, interface 100 can receive and display text characters, symbols and/or colors in various input compartments/cells to mark occurrence or a characteristic associated with a patient care event or patient condition. In an aspect, input compartments associated with various patient events or conditions are filled with a color to indicate occurrence and/or a characteristic of the patient care event or condition at a time associated with the input compartment. Different colors can be used to distinguish between different patient care events or conditions and/or characteristics of the patient care events or conditions. For example, in interface 100, each cell corresponding to an amount of time passed following admittance of the patient is filled with blue, each cell corresponding to an amount of time passed following ROM is filled with green, each cell corresponding to an amount of time passed following administration of cytotec is filled with yellow, etc.

In an aspect, different colors or color shades can be employed to indicate a characteristic of the information represented thereby. For example, different shades of yellow can be employed to distinguish between different degrees of dilation. As seen in interface 100, as dilation increase from 2 cm to 9 cm, the shade of yellow associated with each cell including the dilation information intensifies. A change in color from bright yellow to lime green in cell 148 can be used to indicate dilation is complete. In another example, different input colors can be employed to distinguish between different stages associated with labor (e.g., stage I is marked by light green, stage II marked by light purple) and different categories associated with labor (e.g., category I is marked by pink and category II is marked by red).

Input can be provided within a single cell, (or portion of a single cell), to mark a fixed event or condition or a characteristic associated with on ongoing event or condition at a specific point or period of time. For example, cell 156 includes color data and text data identifying a degree of dilation at time 12 hours. In another example, cell 154 includes color data and text data identifying an amount of time (e.g., 30 seconds) associated with heart rate acceleration between 8 and 12 hours following patient admittance. In yet another example, cell 158 includes text data identifying a maternal heart rate at 4 hours after admittance.

Where a patient care event or patient condition is ongoing, sequential cells or compartments of a row corresponding to the patient care event and the times during which the patient care event or condition occurs, are filled with a same solid or color, resulting in the creation of a horizontal color bar. These color bars can establish a visual timeline for the duration of a particular patient care event or condition. For example, color bar 132 corresponds to an amount of time elapsed following admittance of the patient, color bar 134 corresponds to an amount of time elapsed following ROM, color bar 136 corresponds to an amount of time elapsed following administration of cytotec, color bar 138 corresponds to an amount of time elapsed following administration of pitocin, color bar 140 corresponds to an amount of time elapsed while the patient was in stage I of labor, color bar 142 corresponds to an amount of time elapsed while the patient was in stage II of labor, color bar 144 corresponds to an amount of time elapsed while the patient was in category I of labor, color bar 146 corresponds to an amount of time elapsed while the patient was in category II of labor, color bar 150 correspond to an amount of time where the maternal blood pressure was high (e.g., above 145/90), and color bar 152 corresponds to an amount of time elapsed following administration of magnesium.

In an aspect, data fields or rows associated with ongoing patient conditions/events are configured to automatically populate cells associated therewith as time progresses. In particular, after data is received at a time indicating onset or occurrence of a patient care event or condition, cells associated with the patient care event or condition following the time the data is initially received can automatically be filled (with a same color) to indicate an amount of time elapsed following onset of the patient care event or patient condition and/or an amount of time during which the patient event or condition persists. For example, when a patient is admitted, a user can mark or fill the initial cell at time 0 hours and field admittance 104 (or otherwise provide input data indicating when the patient was admitted for association/display in admittance field 104). Respective cells associated with the admittance field/row 104 can then auto populate as time progresses with data (e.g., the color blue) until data is received indicating the patient has been released. According to this aspect, a clock can be employed to detect passage of time in association with auto filling of cells.

In addition, key information associated with a color bar can be displayed in text at the tip of the color bar. As seen in interface 100, color bar 132 includes text at the tip thereof indicating the patient has been admitted for 24 hours, color bar 134 includes text at the tip thereof indicating it has been 16 since ROM, color bar 136 includes text at the tip thereof indicating cytotec has been applied 8 hours ago, etc. In an aspect, the information included within a color bar can dynamically update to reflect progression of the color bar over time. For example, information identifying an amount of time represented by the color bar can be included at the tip of the color bar and be automatically updated or calculated based on a current point in time.

In another aspect, data fields associated with ongoing patient conditions/events are configured to automatically populate cells associated therewith as time progresses until new input indicating a change in the patient condition/event is received. For example, when a patient enters stage I of labor, a user can mark or fill the initial cell at time 0 hours and data field/row stage 112 (or otherwise provide input data indicating when the patient entered stage I of labor for association/display in stage field 112). Respective cells associated with data field/row stage 112 can then auto populate as time progresses with data (e.g., the color light green) until new data is received indicating the patient is no longer in stage I of labor. For example, regarding generation of interface 100, after the passage of 20 hours time, new data can be received indicating the patient has entered stage II of labor. At this point, the color bar 140 associated with stage I of labor is fixed and a new color bar 142 associated with stage II of labor is initiated.

The various data fields 104-128 of interface 100 can be pre-defined or defined based on user input. For example, a graphical user interface (e.g., interface 100) that facilitates tracking a patient undergoing labor can include a plurality of pre-defined data fields know to be relevant to a course of care of a patient undergoing labor. In another example, a graphical user interface that facilitates tracking a patient suffering from acute coronary syndrome can include a plurality of pre-defined data fields know to be relevant to a course of care of a patient suffering from acute coronary syndrome. In yet another example, a user can provide input defining respective data fields associated with a course of patient care. According to this example, a user can add any number N of data fields to correspond to a relevant patient condition or patient care event.

In an aspect, data fields can be added (e.g., by a user or automatically) as needed over the course of patient care. For example, each time a new drug is administered to the patient, a new data field corresponding to the drug can be added. In another aspect, a patient care tracking interface (e.g., interface 100) can be configured to add data fields in response to occurrence of a patient care event/condition or characteristic of the event/condition. For example, when a new patient condition occurs (e.g., as determined by a medical caregiver or system configured to monitor patient conditions), a patient tracking tool responsible for generating interface 100 can create a new data field to correspond to the patient condition. The patient tracking tool can also automatically fill a cell included in the data field corresponding to a time associated with the new patient condition. In another example, the patient tracking tool can add data fields over the course of care based on anticipated patient conditions or events. For example, the patient tracking tool can determine, based on occurrence of condition "ABC" at time TA, condition "XYZ" is likely to occur at time $T_B$, (where time $T_B$ follows time TA). The patient tracking tool can then generate a new data field corresponding to condition "XYZ." In yet another example, the patient tracking tool can automatically add data fields based on a predefined relationship between a data field selected for a patient care event or patient condition and other patient care events or patient conditions. For example, where a data field is added that corresponds to a patient care event "DEF," data interacting tool can be configured to add one or more additional sub-data fields related to patient care event "DEF."

In addition to data fields corresponding to patient care events or patient conditions, interface 100 can be configured to automatically add columns corresponding to new points or segments of time as the points or segments of time occur. For example, each time a new period of 4 hours passes or is initiated, interface 100 can generate a new column corresponding to the new period of 4 hours. It should be appreciated that columns associated with the horizontal timeline axis can be associated with various increments of time and are not limited to 4 hour increments. For example, columns associated with axis 102 can respectively correspond to sequential time segments of 15 minutes, 30 minutes, one hour, two hours, etc.

As previously noted, in one aspect, a user can select a specific row, column or cell and input data (e.g., a color, text, a symbol) into the specific row, column or cell. For example, a user can select a cell corresponding to a patient care event or condition occurring at a particular point in time and input data or fill the cell to identify occurrence and/or a characteristic of the patient care event or condition. In another example, only those cells associated with a current point in time can be activated for selection/receipt of input. According to this example, a user cannot go back in time and change previously entered data and/or skip ahead in time to input data. Also according to this example, because data input for a particular data field will be automatically associated with a cell corresponding to a current point in time, rather than selecting the cell, the user can merely select the data field for which input is desired. For example, a user can provide input (or the input can be received automatically from a medical device or other device) indicating the patient's current temperature is 37.2° C. Based on timing of receipt of the input, a logging component associated with interface 100 can automatically enter the input into the appropriate cell located at a column corresponding to the timing of receipt and a row or data input field corresponding to temperature (e.g., data input field/row 124 at column 16 hours). In an aspect, in order to facilitate efficient entry of data into interface 100, one or more data fields or cells can be associated with a drop down menu that is activated upon selection of the data field or cell. The drop down menu can provide various data input options that can be selected for entry into the data field or cell.

FIG. 2 presents an example device 200 having a patient monitoring module 204 for generating a patient tracking interface (e.g., interface 100 and the like) in accordance with aspects and embodiments described herein. Device 202 can include memory 220 for storing computer executable components and instructions and processor 222 to facilitate operation of the instructions (e.g., computer executable components and instructions) by system device 202. Repetitive description of like elements employed in respective embodiments of systems, device, and interfaces described herein are omitted for sake of brevity.

As used in this disclosure, the terms "content consumer" or "user" refers to a person, entity, system, or combination thereof. For example, the term user is often employed herein to refer to a medical worker that provides input for inclusion in a patient tracking interface. Device 202 can include any suitable computing device associated with a user and configured to execute patient monitoring module 204 and/or provide a patient tracking interface (e.g., interface 100 and the like) in accordance with aspects described herein. For example, device 202 can include but is not limited to, a desktop computer, a laptop computer, a server, a cellular phone, a smartphone, a tablet personal computer (PC), or a personal digital assistant (PDA).

Patient monitoring module 204 is configured to generate a patient tracking interface (e.g., interface 100) as described herein. Device 202 can include presentation component 218 to display the patient tracking interface (e.g., via a display screen) to a user. For example, patient monitoring module 204 can generate patient tracking interface 100 (and the like) at device 202 and present interface 100 via a display screen associated with device 202. Additional examples of patient tracking interfaces in accordance with aspects described herein are presented in FIGS. 3-8B.

Patient monitoring module 204 can include reception component 206, interface component 208, logging component 220, time component 212 and security component 214. Interface component 206 is configured to generate an interface that facilitates tracking a course of care of a patient, such as patient tracking interface 100. The various features of interfaces capable of generation by interface component 206 are described in association with the example interfaces provided in FIG. 1 and FIGS. 3-8B. However common features of the various interfaces capable of generation by interface component 206 include a plurality of input compartments defined by a first axis having columns corresponding to sequential points in time and a second axis having rows respectively corresponding to patient care events or patient conditions associated with a course of patient care.

Reception component 208 is configured to receive input regarding a patient care event or condition that occurred over a course of patient care for which a patient tracking interface is configured to track. For example, reception component 208 can receive input directed towards a particular cell/compartment of a patient tracking interface indicating occurrence and/or a characteristic of a patient care event or patient condition represented by the cell/compartment at a time corresponding to the cell/compartment. In another example, reception component 208 can receive input merely identifying occurrence and/or a characteristic of a patient care event or patient condition. According to this example, based on the received input, logging component 210 can provide data (e.g., text, a color, a symbol) into the appropriate cell or cells of a patient tracking interface that correspond to the patient care event or patient condition at the time at which the input was received. The data can include text, a fill color, and/or a symbol representative of the occurrence and/or a characteristic of the patient care event or patient condition. In an aspect, where input is received for a new patient care event or condition that is not represented by the patient tracking interface, interface component 206 can automatically generate a new data input field/row corresponding to the new patient care event or condition. Reception component 208 can also receive user input defining a data input field/row for inclusion in a patient tracking interface and/or defining time segments for association with respective columns of the patient tracking interface.

Information received by reception component 206 can be provided by a user or a remote device (e.g., a remote medical device). For example, a user can provide input data directly into a row, column or cell/compartment of a patient tracking interface. In another example, a user can merely provide information indicating occurrence and/or a characteristic of a patient care event or patient condition. In another example, information identifying occurrence and/or a characteristic of a patient care event or patient condition can be received from a medical device associated with the patient. According to this example, the medical device can be configured to send information identifying occurrence and/or a characteristic of the patient care event or patient condition to reception component. In an aspect, reception component 206 is configured to receive information regarding occurrence and/or a characteristic of a patient care event or patient condition in real time over the course of patient care.

Logging component 210 is configured to fill one or more input compartments of a patient tracking interface (e.g., interface 100 and the like) in response to input received by reception component. In an aspect, logging component 210 can fill one or more input compartments of a patient tracking interface that respectively corresponding to a point or period of time associated with occurrence of a patient care event or patient condition in response to reception input identifying occurrence of the patient care event or patient condition. For example, in response to reception of information indicating intravenous magnesium was started on the patient at time of 1:23 pm, logging component 210 can input data into a cell/compartment of the patient tracking interface corresponding to a data input field/row for intravenous magnesium at time of 1:23 pm. The data can include text, color, and/or a symbol indicating that intravenous magnesium has been administered.

In another aspect, logging component 210 can fill one or more input compartments of a patient tracking interface that respectively corresponding to a point or period of time associated with occurrence of a patient care event or patient condition with data representative of a characteristic of the patient care event or patient condition in response to reception of input identifying the characteristic. For example, in response to reception of information identifying a degree of dilation of 3 cm of a patient at time 12:45 pm, logging component 210 can input data into a cell/compartment of the patient tracking interface corresponding to a data input field/row for dilation at time 12:45 pm. The data can include text, color, and/or a symbol indicating the patient has a degree of dilation of 3 cm.

Time component 212 is configured to track progression of time over the course of care. For example, time component 212 can include a clock that identifies a time when patient care begins and tracks passage of time over the course of care. Time component 212 can determine a current point in time, and/or an amount of time passed following initiation of the course of care, associated with receipt of information identifying occurrence and/or a characteristic of a patient care event or patient condition. In turn, logging 210 can determine the appropriate area of a timeline (e.g., column) to include data identifying the occurrence and/or a characteristic of the patient care event or patient condition based in part on a time of receipt of the input.

In an aspect, received input regarding a patient care event or patient condition identifies a time of onset of a patient care event or patient condition that is ongoing. According to this aspect, time component 212 can track progression of time over the course of care following receipt of the input and logging component 208 can automatically fill input compartments of a row corresponding to the patient care event or patient condition over the course of care until new input is received that identifies a change in the patient care event or patient condition or until the course of patient care ends. For example, following receipt of data indicating that a patient has entered stage I of labor, logging component 208 can automatically fill compartments/cells of a row corresponding to stage I of labor to indicate that the patient is currently in stage I of labor as time progresses until new information is received that the patient is not longer in stage I of labor. In another aspect, following receipt of data indicating that a patient care event or patient condition (e.g., ROM) has occurred, logging component 208 can automatically fill compartments/cells of a row corresponding to the patient care event or patient condition to indicate an amount of time elapsed following occurrence of the patient care event or patient condition.

Security component 214 is configured to restrict access to a patient tracking interface and/or restrict devices/users from which information can be received for input into a patient tracking interface. For example, security component 214 can provide a authentication/authorization mechanism that allows only authorized users (medical staff) to access and/or manipulate data associated with a patient tracking interface (e.g., interface 100 and the like).

Device 202 can include presentation component 218 to present or display a patient tracking interface generated/configured by interface component 208. Presentation component 218 can present a patient tracking interface (e.g., interface 100 and the like) for use with any suitable type of computing device, for example a mobile phone, a tablet computer, a desktop computer, a server system, a personal computer, a cable set top box, satellite set top box, a television set, or an internet-enabled television. The respective devices listed above often have different capabilities and limitations (e.g., screen size, decoders . . . ). In an aspect, presentation component 120 can provide presentation options in accordance with different device capabilities or limitations. For example, data rendering capabilities may be more limited in a mobile device (e.g., a smart-phone) than in a fixed computing device (e.g., a desktop computer). In addition, because displays of various mobile devices are often smaller than displays in fixed computing devices, it may be possible only to display a relatively small amount of information at any given time on a mobile device.

In view of the above, presentation component 218 can present patient tracking interfaces generated/configured by interface component 208 in various formats and/or in accordance with various display mediums. In particular, presentation component 218 can adapt and optimize display of options and content based on respective rendering device capabilities (e.g., based on screen size, screen resolution, input capabilities of the devices, processing capabilities etc.). For example, presentation component 208 can adapt the size, shape, and number of columns, rows and/or cells displayed or included in a patient tracking interface based on the size and orientation of a display screen of a device at which the patient tracking interface is displayed.

Input component 216 is configured to facilitate user interaction with a patient tracking interface displayed at device 202. In particular, input component 216 can be configured to receive commands from an input device associated with device 202 (e.g., a controller, a keyboard, a mouse, a touch screen, voice recognition input device, a gesture recognition input device, etc., (not shown)), and interpret those commands to facilitate user interaction with a patient tracking interface displayed at device 202. For example, input component 216 can receive commands from a user to define a data field or row, to add a data field or row, to define time segments for representation by respective columns of the timeline, to add columns, or to provide data input to fill cells of the patient tracking interface (e.g., with text, a color, a symbols, etc.). For example, input component 216 can include a touch screen display that allows a user to touch various parts of a patient tracking interface to provide data input associated with the various parts. In another example, input component 216 can include a voice recognition input device that can identify and interpret voice commands regarding filling a patient tracking interface with data.

FIGS. 3-7 present examples of various graphical user interfaces that facilitate tracking information related to a course of patient care. In particular, FIGS. 3-7 demonstrate an example patient tracking interface as it evolves from a default shell or form in response to receipt of input regarding care of a patient over the course of care of the patient. Although these example interfaces demonstrate tracking patient care events and conditions associated with a course of labor, it should be appreciated that various aspects of the interfaces can be employed to track other type of patient care scenarios. Further, it should be appreciated that the patient care events and conditions monitored in these example interfaces are not intended to limit the scope of possible patient care events and conditions that can be monitored via the subject patient tracking tool. In particular, a data field provided in row of the interfaces described herein can be adapted to correspond to any possible patient care event or condition associated with a course of labor. In addition, one or more of the data fields provided in the respective interfaces can be removed and/or additional data fields can be added. Repetitive description of like elements employed in respective embodiments of systems and interfaces described herein are omitted for sake of brevity.

With reference initially to FIG. 3, presented is an example shell patient tracking interface 300 in accordance with aspects and embodiments described herein. Interface 300 includes a plurality of compartments (e.g., the cells/compartments collectively identified by numeral 312) defined by a first axis 310 having columns corresponding to sequential periods (e.g., 4 hour periods) of time over the course of patient care and a second axis 308 having one or more rows respectively corresponding to one or more patient care events or patient conditions. In particular, row 302 corresponds to admittance of the patient. Rows 304 and 306 include undefined fields. In an aspect, a user can select row 304 and/or row 306 to define a data field for the row associated with a patient care event or patient condition. It should be appreciated that any number N of data fields/rows can be added.

In an aspect, interface 300 can be modified or configured to track any course of patient care that involves caring for a patient over a period of time. According to this aspect, the data fields or rows can be fully or partially defined by a user.

In another aspect, interface 300 can be configured for tracking a specific course of patient care (e.g., labor). According to this aspect, one or more of the data fields/rows can be preconfigured to represent a known patient care event and/or patient condition associated with the specific course of care.

In addition, one or more data fields/rows can be preconfigured for inclusion in interface 300 in response to occurrence of a predetermined event or condition. According to this aspect, information defining relationships between patient care events and patient conditions for a course of patient care, and/or characteristics of the patient care events or conditions (e.g., stored in memory 220), can direct automatic addition of data fields to interface 300 (e.g., by interface component 206). For example, in response to addition/inclusion of a data field to interface 300 corresponding to a first patient care event or patient condition, one or more additional sub-data fields related to or dependent on the first patient care event or condition can be automatically added to interface 300 (e.g., by interface component 206). In another example, in response to receipt of data associated with occurrence and/or a characteristic of a first patient care event or patient condition, one or more additional sub-data fields related to the occurrence or the characteristic of the first patient care event or condition can be added. For instance, if a patient has a temperature above X degrees, based on known factors related to the patient and the course of care, an appropriate medical response can include administration of drug Y. Accordingly, in response to received data indicating the patient has a temperature above X degrees, a data field corresponding to administration of drug Y can automatically be added to interface 300. Still in yet another example, one or more data fields can be automatically added to interface 300 in response to passage of various amounts of time in view of a course of patient care for which the interface is configured to track. For example, in association with a particular course of care, after the patient has been admitted 8 hours, the patient should receive X and Y treatment. Thus in response to passage of 8 hours following admittance, data fields for treatments X and Y can be added to interface 300 automatically (e.g., via interface component 206).

FIG. 4 depicts another exemplary patient tracking interface 400 in accordance with aspects and embodiments described herein. Interface 400 is specifically configured to track the course of care of a patient throughout labor. In an aspect, interface 400 is an extension of interface 300 following admittance of a patient for 8 hours. According to this aspect, default data fields 304 and 306 of interface 300 have respectively been changed to data fields 402 and 404. Data field 402 corresponds to stages of labor and data field 404 corresponds to categories of labor. Stages of labor and categories of labor can include stages and categories of labor associated with a condition of the mother and/or the infant. For exemplary purposes, date input field 402 corresponding to stages of labor indicates a descriptive stage of a state associated with the infant and input field 404 corresponding to categories of labor indicates a descriptive category of a state associated with the mother. In an aspect, data fields 402 and 404 are defined by a user. In another aspect, data fields 402 and 404 are automatically created in response to receipt of input indicating the patient has been admitted and input tailoring interface 400 for tracking labor of a patient.

In an aspect, upon admittance of the patient, information is received indicating she has been admitted, has entered category 1 of labor and her infant is in stage 1. For example, this information can be entered by a medical caregiver. In response to entry of the information, color bars 406, 408 and 410 are respectively initiated or generated (e.g., by logging component 210). Color bars 406, 408 and 410 are configured to represent timelines respectively indicating amount of elapsed time the following admittance of the patient, duration of time the infant is in stage 1, and duration of time the patient is in category 1 of labor. In an aspect, color bar 406 is configured to automatically continue horizontally (e.g., to the right) across interface 400 in response to passage of time until information is received indicating the patient is no longer admitted. Similarly, color bars 408 and 410 can also be configured to automatically continue horizontally (e.g., to the right) across interface 400 until new information is received indicating the infant is no longer in stage 1 or the patient is in category 1 of labor, respectively.

Figure 5:
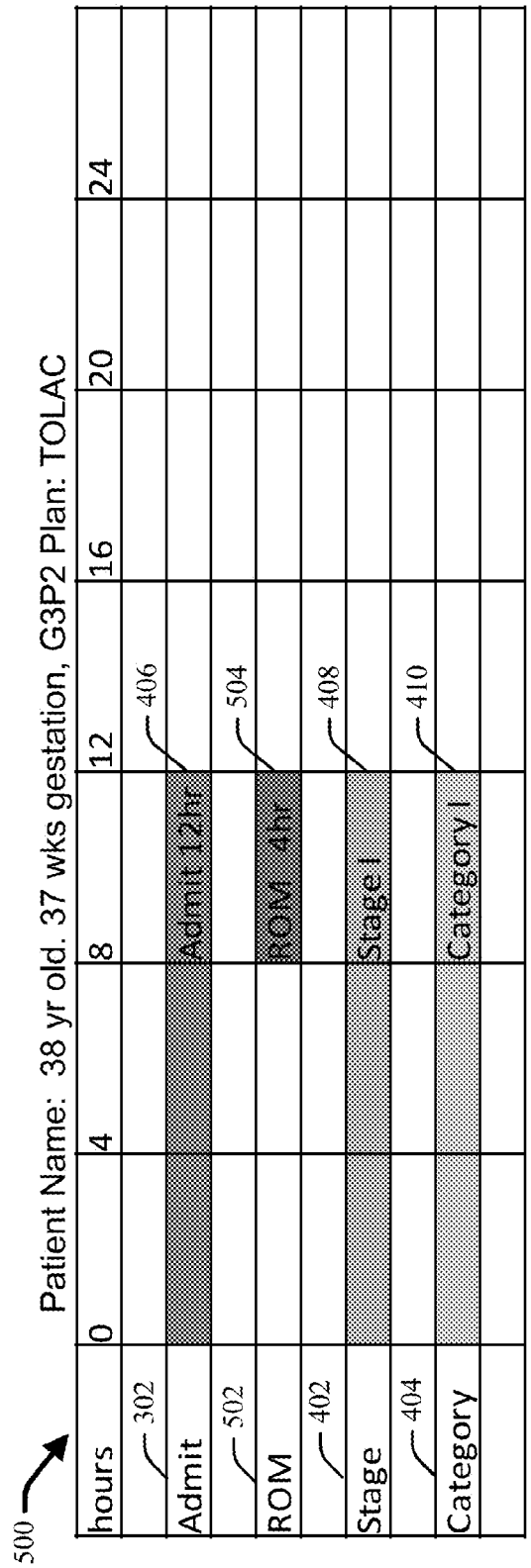
FIG. 5 illustrates a block diagram of another example user interface facilitates tracking and displaying patient information over the course of care in accordance with various aspects and embodiments described herein.

FIG. 5 depicts another exemplary patient tracking interface 500 in accordance with aspects and embodiments described herein. In an aspect, interface 500 is an extension of interface 400 following admittance of the patient for 12 hours. Interface 500 includes a new data field 502 corresponding to ROM. Interface 500 further includes a new color bar 504 indicating that the patient's membranes ruptured following 8 hours of admittance (e.g., or sometime between 8 and 12 hours after admittance). In an aspect, data field 502 and color bar 504 was added to interface 500 based on user input defining and adding the data field and indicating that the patient's membrane ruptured at a time between 8 and 12 hours of time following admittance of the patient. In another aspect, data field 502 and color bar 504 was added to interface 500 in response to receipt of input indicating that the patient's membrane ruptured at a time between 8 and 12 hours of time following admittance of the patient.

As seen when comparing interfaces 400 and 500, color bars 406, 408 and 410 have automatically (e.g., without additional user input) extended horizontally across interface 500 in response to passage of time. In an aspect, color bar 504 is also configured to automatically continue horizontally (e.g., to the right) across interface 500 in response to passage of time until information is received indicating the patient is no longer admitted.

Figure 6:
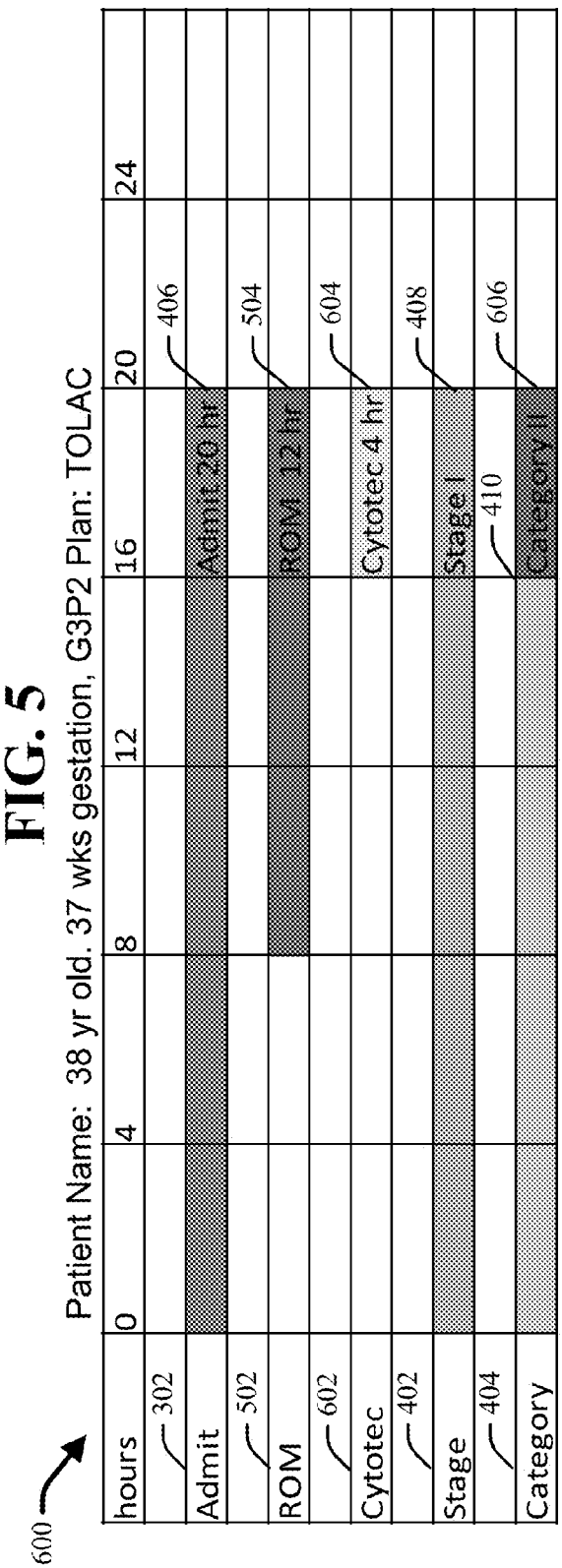
FIG. 6 illustrates a block diagram of another an example user interface facilitates tracking and displaying patient information over the course of care in accordance with various aspects and embodiments described herein.

FIG. 6 depicts another exemplary patient tracking interface 600 in accordance with aspects and embodiments described herein. In an aspect, interface 600 is an extension of interface 500 following admittance of the patient for 20 hours. Interface 600 includes a new data field 602 corresponding to Cytotec. Interface 600 further includes a new color bar 604 indicating that the patient was administered cytotec between 16 and 20 hours following admittance and new color bar 606 indicating the patient has entered category II of labor. In an aspect, data field 602 and color bar 604 was added to interface 600 based on user input defining and adding the data field and indicating that the patient was admitted cytotec between 16 and 20 hours following admittance. In another aspect, data field 602 and color bar 604 was added to interface 600 in response to receipt of input indicating that the patient was administered cytotec between 16 and 20 hours following admittance. In addition, color bar 410 was capped and color bar 606 was initiated in response to receipt of new data indicating the patient has entered category II of labor.

As seen when comparing interfaces 500 and 600, color bars 406, 408, 410 and 504 have automatically (e.g., without additional user input) extended horizontally across interface 600 in response to passage of time. In an aspect, color bar 604 is configured automatically continue horizontally (e.g., to the right) across interface 600 in response to passage of time until information is received indicating the patient is no longer being administered cytotec. Similarly, color bar 606 can be configured to automatically (e.g., to the right) continue across interface 600 in response to passage of time until information is received indicating the patient is no longer in category II of labor.

Figure 7:
FIG. 7 illustrates a block diagram of another example user interface facilitates tracking and displaying patient information over the course of care in accordance with various aspects and embodiments described herein.

FIG. 7 depicts another exemplary patient tracking interface 700 in accordance with aspects and embodiments described herein. In an aspect, interface 700 is an extension of interface 600 following admittance of the patient for 24 hours. Interface 700 includes a new data field 702 corresponding to pitocin. Interface 700 further includes a new color bar 704 indicating that the patient was administered pitocin between 20 and 24 hours following admittance and new color bar 706 indicating the infant has entered stage II. In an aspect, data field 702 and color bar 704 was added to interface 700 based on user input defining and adding the data field and indicating that the patient was admitted pitocin between 20 and 24 hours following admittance. In another aspect, data field 702 and color bar 704 was added to interface 700 in response to receipt of input indicating that the patient was administered pitocin between 20 and 24 hours following admittance. In addition, color bar 408 was capped and color bar 706 was initiated in response to receipt of new data indicating the infant has entered stage II.

As seen when comparing interfaces 600 and 700, color bars 406, 504, 604 and 606 have automatically (e.g., without additional user input) extended horizontally across interface 700 in response to passage of time. In an aspect, color bar 704 is configured automatically continue horizontally (e.g., to the right) across interface 700 in response to passage of time until information is received indicating the patient is no longer admitted. Similarly, color bar 706 can be configured to automatically (e.g., to the right) continue across interface 700 in response to passage of time until information is received indicating the infant is no longer in stage II.

Figure 8B:
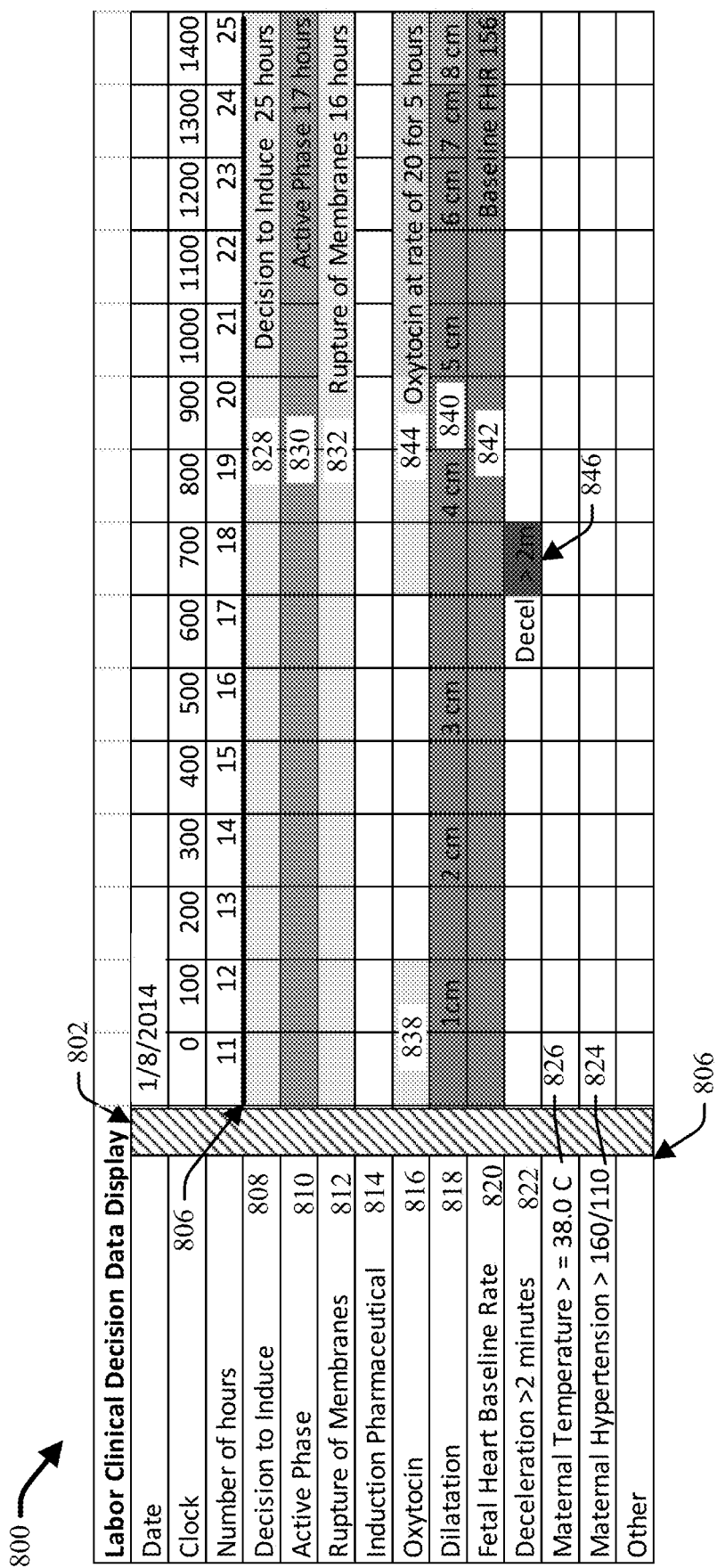

FIGS. 8A-8B, present another example patient tracking interface 800 in accordance with aspects and embodiments described herein. Patient tracking interface 800 depicts a completed interface following tracking of a patient in labor over the course 25 hours and two days. FIG. 8A includes information for the first day (Jan. 7, 2014) and FIG. 8B includes information for the second day (Jan. 8, 2014). It should be appreciated that interface 800 is divided over FIGS. 8A and 8B merely for lack of space due to restrictions in page dimensions. In particular, interface 800 can be displayed as a single continuous chart. Bar 802 is provided as a marker to indicate how interface 800 in FIG. 8A connects to interface 800 in FIG. 8B.

Interface 800 includes a plurality of compartments (defined by a first axis 804 having columns corresponding to sequential hours of time (in military time) and/or sequential hours passed, and a second axis 806 having a plurality of rows respectively corresponding to patient care events and patient conditions. In particular, row 808 corresponds to decision to induce. Data included in row 808 depicts the actual elapsed time from onset of induction. For example, grey color bar 828 marks the elapsed time following the decision to induce. In an aspect, grey color bar 828 moved horizontally across row 808 with each passing hour marked as a fixed point following initial data input indicating the decision to induct at time 1500.

Row 810 corresponds to active phase. Data included in row 810 depicts the actual elapsed time from the beginning of the active phase of labor. For example, green color bar 830 marks the elapsed time following beginning of active phase. In an aspect, green color bar 830 moved horizontally across row 810 with each passing hour marked as a fixed point following initial data input indicating the beginning of active phase at time 2100.

Row 812 corresponds to rupture of membranes. Data included in row 820 depicts the actual elapsed time following rupture of the patients membranes. For example, beige color bar 832 marks the elapsed time following rupture of membranes. In an aspect, beige color bar 832 moved horizontally across row 812 with each passing hour marked as a fixed point following initial data input indicating the rupture of membranes at time 2400.

Row 814 corresponds to induction pharmaceutical. Data included in row 814 depicts blocks of time during which an induction pharmaceutical was administered. For example, yellow bar 834 indicates that a first dose of cytotec was administered beginning at time 1500 and ending at time 1600. Yellow bar 836 indicates a second dose of cytotec was administered beginning at time 2000 and ending at time 2300. In an aspect, various types of induction pharmaceuticals can be administered to a patient. Accordingly, text can also be included in association with data input to row 814 (e.g., the yellow fill) to indicate which induction pharmaceutical was administered. In an aspect, data field/row 814 can include a drop down menu that is displayed upon selection of data field/row 814 and provides options of induction pharmaceuticals to select from for ease of date entry. In another aspect, different induction pharmaceuticals can be associated with different fill colors.

Row 816 corresponds to oxytocin. Data included in row 816 depicts blocks of time during which oxytocin was administered. For example, grey bar 838 indicates that a first dose of oxytocin was administered beginning at time 2300 on Jan. 7, 2014 and ending at time 100 on Jan. 8, 2014. Grey bar 844 indicates a second dose of oxytocin was administered beginning at time 700 and ending at time 1400 on Jan. 8, 2014. In an aspect, an oxytocin is an intravenous drug that can be started and stopped multiple times during the course of labor. Grey bars 838 and 844 can indicate blocks of time when the drug is infusing. Text data indicating the "rate of infusion" can also be included in association with respective fill blocks indicating times when the drug is infused. In an aspect, text data indicating rate of infusion can be included when the rate of infusion is above a threshold rate (e.g., 20 or greater).

Row 818 corresponds to dilation. Data included in row 818 depicts blocks of time during which the patient was dilated. For example, pink color bar 840 indicates blocks of time during which the patient was dilated, beginning at 2300 on Jan. 7, 2014. Text data can be associated with fixed cells indicating a degree of dilation of the patient at the respective times associated with the cells (e.g., 1 cm, 2 cm, 3 cm, etc.).

Row 820 corresponds to fetal heart rate. Data included in row 820 depicts a measured baseline fetal heart rate that includes a fixed number of beats per minute. In an aspect, after the baseline fetal heart rate is selected and/or entered, a color bar (e.g., blue color bar 842) is initiated and moves across row 820 as time passes to indicate what the baseline fetal heart rate was.

Row 822 corresponds to deceleration of the fetal heart rate. Data included in row 822 is entered in response to a deceleration of the fetal heart rate from the baseline fetal heart rate. For example, a color bar (e.g., red color bar 836) can be generated to indicate a fixed time or time period during which the fetal heart rate decelerates. In an aspect, data is entered in row 822 in response to deceleration of the fetal heart rate for a period of time greater than 2 minutes. Information indicating a total amount of time during which the fetal heart rate decelerated can also be included in associated with a fill color in row 822.

Row 824 corresponds to maternal temperature. Data included in row 824 can include a fixed color bar indicating a point in time or period of time during which the maternal temperature exceeded a threshold temperature (e.g., 38° C.). In an aspect, in response to entry of data in row 824, interface 800 can be configured to generate a pop-up display asking the caregiver if an antibiotic was administered. The caregiver can then provide additional input indicating whether an antibiotic was administered or not and what type of antibiotic was administered if an antibiotic was administered. In an aspect, this additional information can be associated with the color block included in row 824 associated with the spike in temperature. In another aspect, in response to an indication that an antibiotic was administered, interface 800 can generate an additional data field/row corresponding to the antibiotic and information regarding administration of the antibiotic can be included in this new data field/row.

Row 828 corresponds to maternal hypertension or blood pressure. Data included in row 828 can include a fixed color bar indicating a point in time or period of time during which the maternal blood pressure (e.g., systolic or diastolic) increased or decreased with respect to threshold values. In an aspect, in response to a second increase in blood pressure above a threshold value, interface 800 can be configured to generate a pop-up display asking the caregiver if intravenous magnesium is to be started. The caregiver can then provide additional input indicating whether intravenous magnesium was administered or not. In an aspect, this additional information can be associated with row 828 where data is provided indicating the rise in blood pressure. In another aspect, in response to an indication that intravenous magnesium was started, interface 800 can generate an additional data field/row corresponding to intravenous magnesium and a color bar can be generated in this additional data field/row indicating the amount of time intravenous magnesium was provided.

Figure 9:
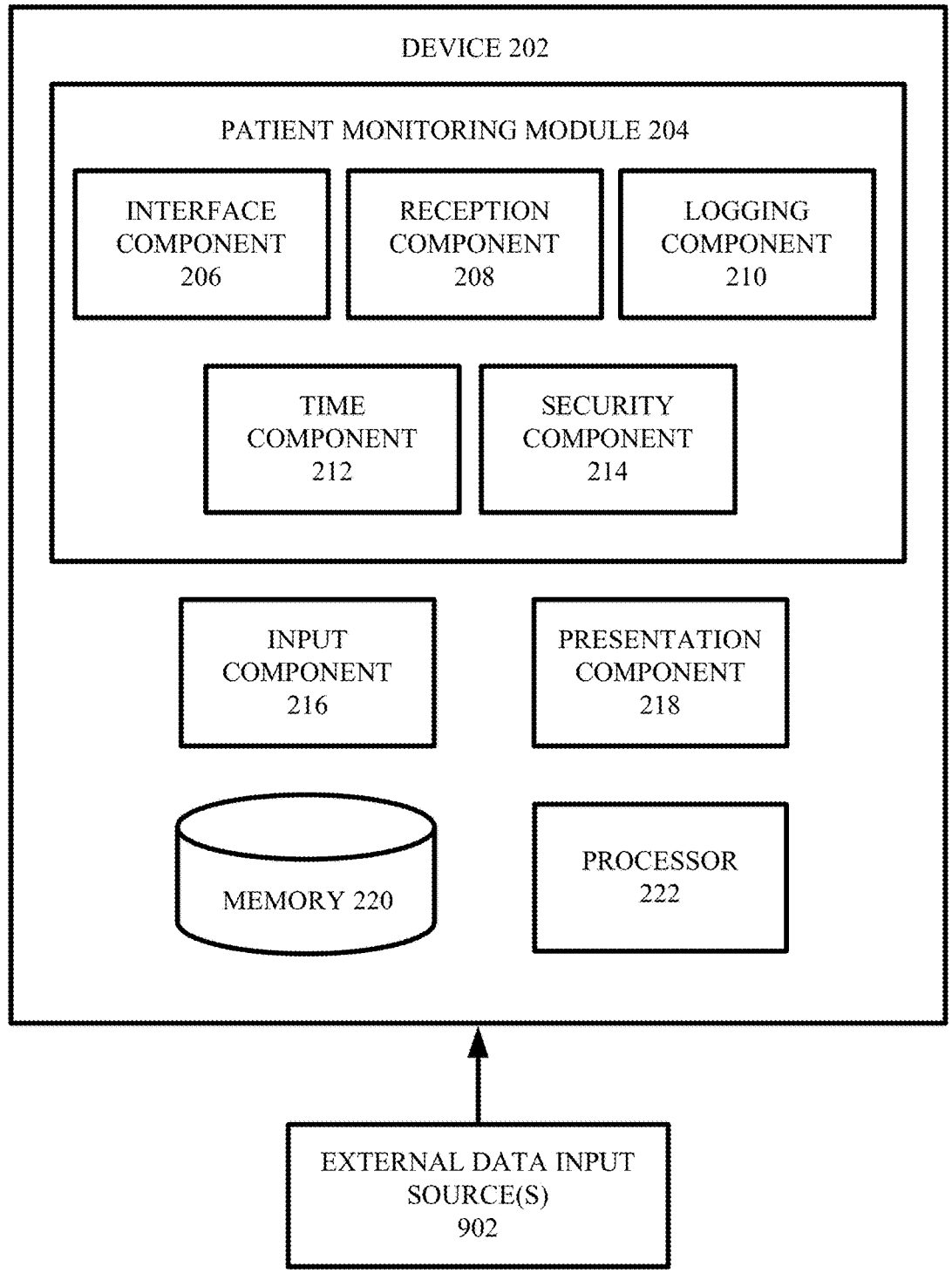
FIG. 9 presents another example system that facilitates tracking and displaying patient information over the course of care in accordance with various aspects and embodiments described herein.

FIG. 9 presents an example system 900 for generating and presenting a patient care tracking interface in accordance with aspects and embodiments described herein. Repetitive description of like elements employed in respective embodiments of systems and interfaces described herein are omitted for sake of brevity.

System 900 includes device 202 and one more external data input sources 902. As previously noted, data input received by reception component 208 can be received from a user (e.g., a medical caregiver) and/or an external device, such as a medical device. For example, a user can input data, (e.g., via input component 216) directly into a patient tracking interface generated by interface component 206 using various input devices (e.g., a touch screen, soft keys, a keypad/keyboard, voice recognition software, etc.). In an aspect, the user can employ a remote device to provide data to reception component 208. According to this aspect, an external data source 902 can include a remote control or remote device that allows a user to send (e.g., either via a wired or wireless data connection) data input to patient monitoring module 204 for entry into a patient tracking interface. For example, the user can employ a remote tablet computer or smartphone to wirelessly transmit data for input to a patient tracking interface via a local area network (LAN).

In another aspect, an external data input source 902 can include a remote medical device associated with the patient. The remote medical device can sense patient conditions/events and send sensed data input to patient monitoring module 204 for input to a patient tracking interface generated by interface component 206 and configured to track a course of care of the patient. The medical device can send data to patient monitoring module 204 via a wired or wireless data connection. In an aspect, the medical device can send the data via a LAN, a personal area network (PAN, e.g., using near field communication, Bluetooth™ communication, etc.), or a wide area network (WAN). Some exemplary medical devices that can automatically provide data input for entry into a patient tracking interface generated by interface component 206 can include but are not limited to: a vital signs monitoring device, a heart monitor device, a pulse oximeter device, a maternal contraction monitor device, a capnograph, a blood gas monitor device, and a respiratory assistance device.

Figure 10:
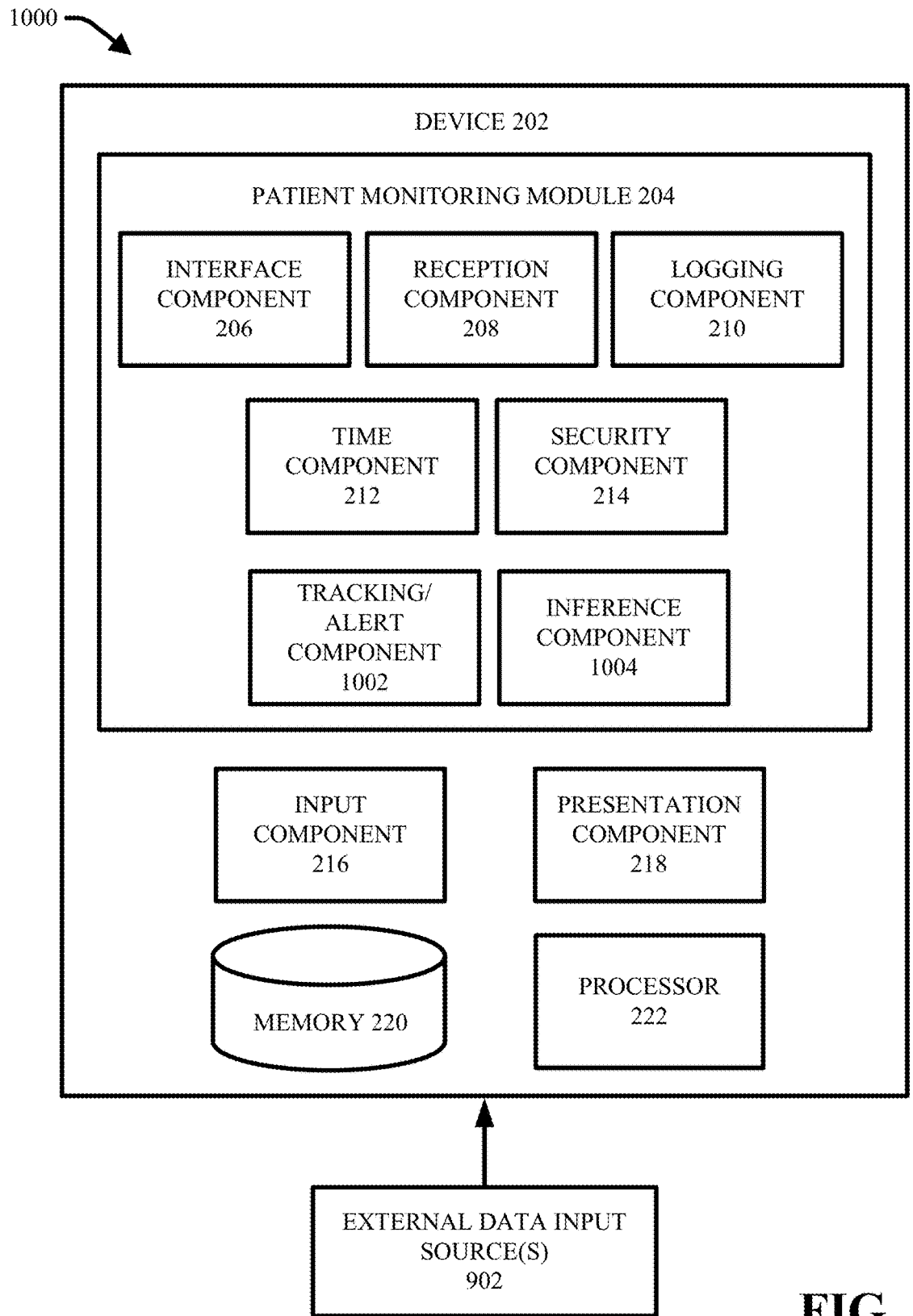
FIG. 10 presents another example system that facilitates tracking and displaying patient information over the course of care in accordance with various aspects and embodiments described herein.

FIG. 10 presents another example system 1000 for generating and presenting a patient care tracking interface in accordance with aspects and embodiments described herein. System 1000 is similar to system 900 with the addition of tracking/alert component 1002 and inference component 1004 to patient monitoring module 204. Repetitive description of like elements employed in respective embodiments of systems and interfaces described herein are omitted for sake of brevity.

Tracking/alert component 1002 is configured to analyze a patient tracking interface based on data entered therein, a course of patient care, and a current point in time to facilitate determining or inferring clinical decisions associated with caring for the patient. In particular, tracking/alert component 1002 can employ various algorithms and information sources that define relationships between patient conditions, patient care events, and a course of patient care to determine or infer clinical decisions regarding caring for the patient and/or to determine or infer issues associated with a condition of the patient.

In an aspect, tracking/alert component 1002 can determine or infer when data is missing from a patient tracking interface regarding a patient care event or patient condition based on relationships between patient care events and/or patient care conditions, a course of patient care, and a current point in the course of the patient care. In response to a determination of missing data regarding a patient care event or patient condition, tracking/alert component 1002 can call attention to a medical caregiver to perform the patient care event and/or check and enter information regarding the patient condition.

For example, tracking/alert component 1002 can determine or infer that based on a course of patient care and a current point in time, data should have been received regarding occurrence of patient care event "WRT." Accordingly, patient tracking/alert component can notify a medical caregiver to perform patient care event "WRT" and enter data regarding performance of the patient care event. In another example, tracking/alert component 1002 can determine or infer that based on data received indicating patient care event "UYT" was performed, information regarding patient condition "345" should have been received. Accordingly, patient tracking/alert component 1002 can notify a medical caregiver to check patient condition "345" and enter data regarding the patient condition. In yet another example, tracking/alert component 1002 can determine or infer that based on data indicating a patient condition has fallen below an unsatisfactory level, information regarding performance of a patient care event "JHG" should have be received. Accordingly, patient tracking/alert component can notify a medical caregiver to perform patient care event "JHG" and enter data regarding performance of the patient care event.

In another aspect, tracking/alert component 1002 can determine or infer issues associated with a patient condition based on relationships between patient care events and/or patient care conditions, a course of patient care, and a current point in the course of the patient care. For example, patient tracking/alert component 1002 can analyze data entered into a patient tracking interface and infer or determine that based on the collective information, the patient is in an unsatisfactory state. For instance, patient tracking/alert component 1002 can determine or infer that based on data regarding various vital signs of the patient and/or the infant and information indicating drug "XCR" was administered, the patient should be responding in a different manner. In response to a determination of an unsatisfactory patient state based on data received or entered into a patient tracking interface, tracking/alert component 1002 can call attention to a medical caregiver and notify the medical caregiver of the unsatisfactory state of the patient and the basis for the determination that the patient is in an unsatisfactory state.

In an exemplary embodiment, tracking/alert component 1002 can monitor various tracked patient care event and tracked conditions of the patient and infant to determine when a cesarean section (C-section) should be performed. For example, tracking/alert component 1002 can determine, (using various preconfigured algorithms defining relationships between patient care events and conditions/states of the mother and infant), that based on a current state of the mother and/or infant and based on previous patient care events and conditions leading up to the current point in time (e.g., including time elapsed associated with patient care events and conditions), that a C-section should be performed.

Tracking/alert component 1002 can employ various techniques to notify a medical caregiver regarding missing data from a patient tracking interface and/or regarding an issue associated with a state or condition of the patient. For example, patient tracking/alert component 1002 can highlight a data field/row or cell associated with missing information to call attention of the medical caregiver to that data field/row and indicate that information is missing therefrom. In another example, the patient tracking alert component 1002 can cause the data field/row or cell to flash. In an aspect, where the missing information is associated with a patient care event or patient condition for which a data field/row is not provided in the patient tracking interface, tracking/alert component 1002 can instruct interface component to create or add the data field/row.

In another example, tracking/alert component 1002 can sound an alarm to notify a medical caregiver regarding missing data from a patient tracking interface and/or regarding an issue associated with a state or condition of the patient. In yet another example, tracking/alert component 1002 can send a notification message to the medical caregiver (e.g., in the form of an electronic message such as a text message, an email, or other form of electronic message) regarding missing data from a patient tracking interface and/or regarding an issue associated with a state or condition of the patient.

Inference component 1004 is configured to provide for or aid in various inferences or determinations associated with aspects of patient monitoring module. For example, inference component 1004 can infer when interface component 208 should add an additional data field/row for a patient care event or patient condition based on relationships between patient care events and/or patient care conditions, a course of patient care, and a current point in the course of the patient care. In another example, inference component 1004 can facilitate tracking/alert component 1002 with various inferences regarding identifying missing data from a patient tracking interface and/or determining an issue associated with a state or condition of the patient. In aspect, all or portions of device 202 can be operatively coupled to inference component 1002. Moreover, inference component 1002 can be granted access to all or portions of external systems/sources (e.g., external data input sources 902 and other external systems).

In order to provide for or aid in the numerous inferences described herein, inference component 1002 can examine the entirety or a subset of the data to which it is granted access and can provide for reasoning about or infer states of the system, environment, etc. from a set of observations as captured via events and/or data. An inference can be employed to identify a specific context or action, or can generate a probability distribution over states, for example. The inference can be probabilistic—that is, the computation of a probability distribution over states of interest based on a consideration of data and events. An inference can also refer to techniques employed for composing higher-level events from a set of events and/or data.

Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 11:
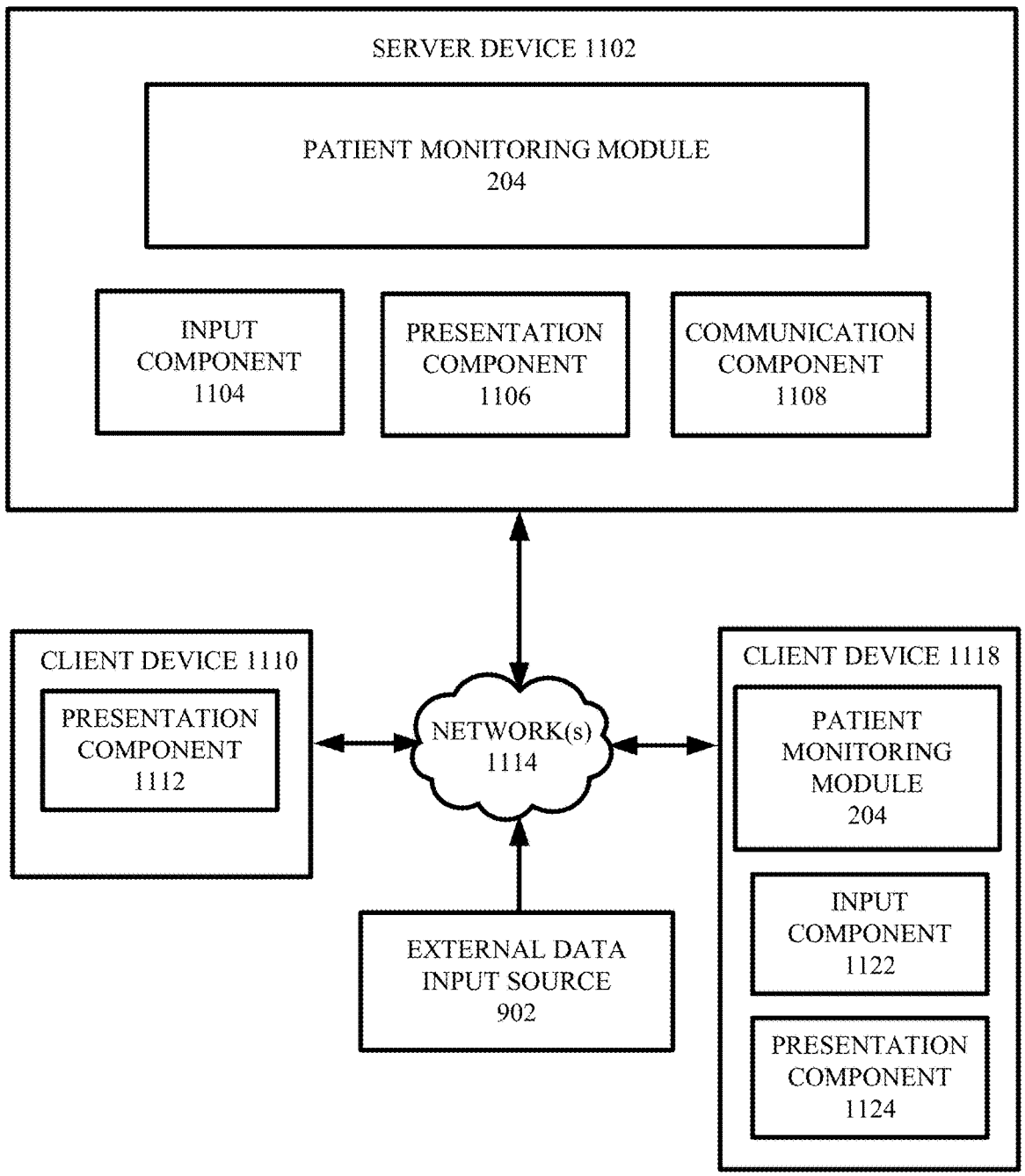
FIG. 11 presents another example system that facilitates tracking and displaying patient information over the course of care in accordance with various aspects and embodiments described herein.

FIG. 11 presents another example system 1100 for generating and presenting a patient care tracking interface in accordance with aspects and embodiments described herein. Repetitive description of like elements employed in respective embodiments of systems and interfaces described herein are omitted for sake of brevity.

Similar to systems 900 and 1000, system 1100 includes a device (e.g., server device 1102 having a patient monitoring module 204 and one or more external data input sources 902. Server device 1102 can include similar features and functionalities as device 202. For example, server device 1102 can input component 1104 and presentation component

1106. Input component 1104 and presentation component 1106 can operate in accordance with input component 216 and presentation component 218, respectively. However, unlike device 202 of systems 900 and 1000, server device 1102 can include communication component 1108. Communication component 1108 is configured to make one or more aspects of patient monitoring module 204 available to one or more other devices (e.g., client device 1110 and/or client device 118) via one or more networks 1114. Network(s) 1114 can include wired and wireless networks, including but not limited to, a cellular network, a wide area network (WAD, e.g., the Internet), a local area network (LAN), or a personal area network (PAN). For example, client device 1118 can communicate with media provider server device 1102 (and vice versa) using virtually any desired wired or wireless technology, including, for example, cellular, WAN, wireless fidelity (Wi-Fi), Wi-Max, WLAN, and etc.

For example, server device 1102 can configure and/or generate a patient tracking interface (e.g., interface 100 and the like) and provide other devices (e.g., client device 1110 and client device 1118) access to the interface via a network 1114. The other devices can display the interface via a presentation component (e.g., presentation component 1112 or 1124 of devices 1110 and 1118 respectively) provided thereon. For example, presentation component 1112 and/or 1124 can access a patient tracking interface configured and stored at the server device 1102 using a browser or web application associated therewith.

In an aspect, users of the other devices can merely view a patient tracking interface hosted by server device 1102 via a network. For example, client device 1110 can view, via a network 1114 using presentation component 1112, a patient tracking interface generated at the server device 1102 as it is updated in real time. In another aspect, users of other devices can interact with a patient tracking interface hosted by server device 1102. For example, client device 1118 can include a client version of patient monitoring module 204 and an input component 1122. According to this example, a user of client device can provide data for input (e.g., via input component) into a patient tracking interface that is generated/configured at both the client device 1118 and the server device 1102. The patient tracking interface at both devices can be updated to reflect the same data input in real time.

In another aspect, communication component 1108 can be configured to transmit received data input associated with a patient tracking interface generated by patient monitoring module to another device (e.g., client device 1110 and/or client device 1118). In response to transmission, the other can be device is configured to generate the patient tracking interface.

Figure 12:
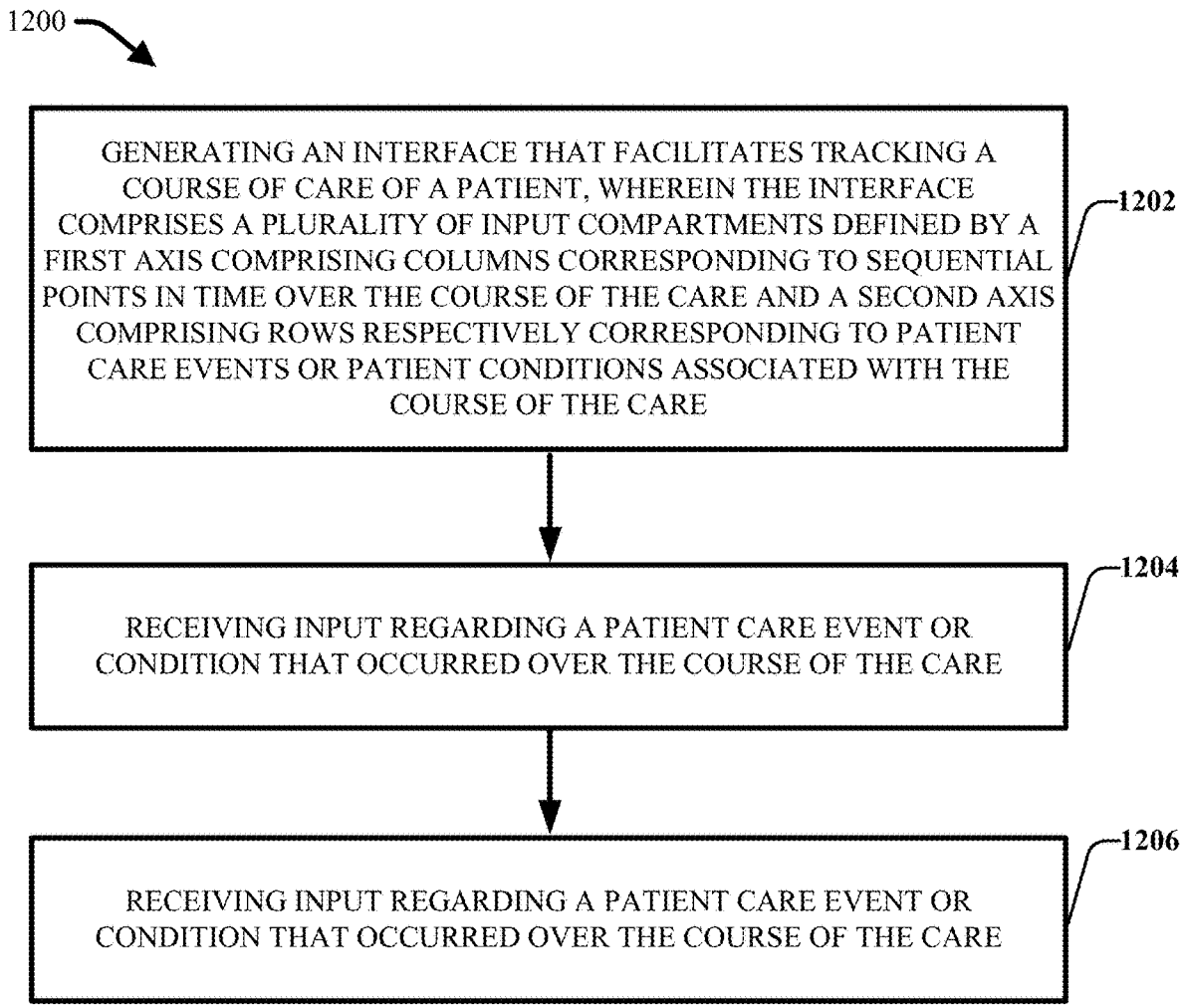
FIG. 12 illustrates a flow chart of an example method for tracking and displaying patient information over the course of care in accordance with various aspects and embodiments described herein.
Figure 13:
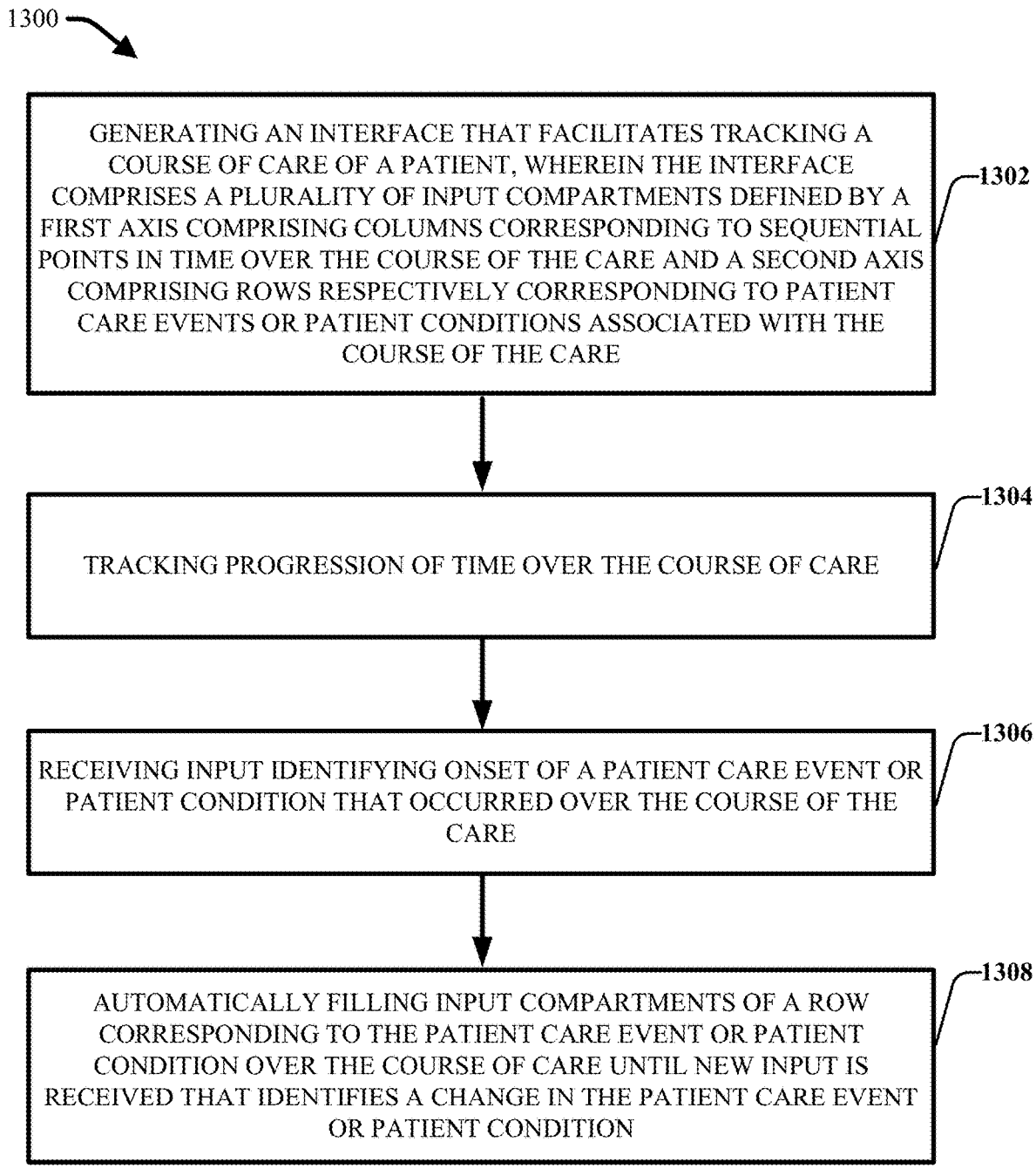
FIG. 13 illustrates a flow chart of an example method for tracking and displaying patient information over the course of care in accordance with various aspects and embodiments described herein.

In view of the example systems/interface described herein, example methods that can be implemented in accordance with the disclosed subject matter can be further appreciated with reference to flowcharts in FIGS. 12-13. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from that shown and described herein. For example, a method disclosed herein could alternatively be represented as a series of interrelated states or events, such as in a state diagram. Moreover, interaction diagram(s) may represent methods in accordance with the disclosed subject matter when disparate entities enact disparate portions of the methods. Furthermore, not all illustrated acts may be required to implement a method in accordance with the subject specification. It should be further appreciated that the methods disclosed throughout the subject specification are capable of being stored on an article of manufacture to facilitate transporting and transferring such methods to computers for execution by a processor or for storage in a memory.

FIG. 12 illustrates a flow chart of an example method 1200 for generating and presenting a patient tracking interface in accordance with aspects and embodiments described herein. At 1202, an interface is generated that facilitates tracking a course of care of a patient (e.g., via interface component 206). The interface includes a plurality of input compartments defined by a first axis having columns corresponding to sequential points in time over the course of the care and a second axis having rows respectively corresponding to patient care events or patient conditions associated with the course of the care. At 1204, input is received regarding a patient care event or condition that occurred over the course of the care (e.g., via reception component 208). At 1206, one or more input compartments respectively corresponding to a point or period of time associated with occurrence of the patient care event or patient condition are filled in response to reception of the input.

FIG. 13 illustrates a flow chart of another example method 1300 for generating and presenting a patient tracking interface in accordance with aspects and embodiments described herein. At 1302, an interface is generated that facilitates tracking a course of care of a patient (e.g., via interface component 206). The interface includes a plurality of input compartments defined by a first axis having columns corresponding to sequential points in time over the course of the care and a second axis having rows respectively corresponding to patient care events or patient conditions associated with the course of the care. At 1304, progression of time over the course of care is tracked (e.g., via time component 212). At 1306, input is received identifying onset of a patient care event or patient condition that occurred over the course of the care (e.g., via reception component 208). At 1308, input compartments of a row corresponding to the patient care event or patient condition are automatically filled over the course of care until new input is received that identifies a change in the patient care event or patient condition.

Example Operating Environments

The systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which may be explicitly illustrated in this disclosure.

Figure 14:
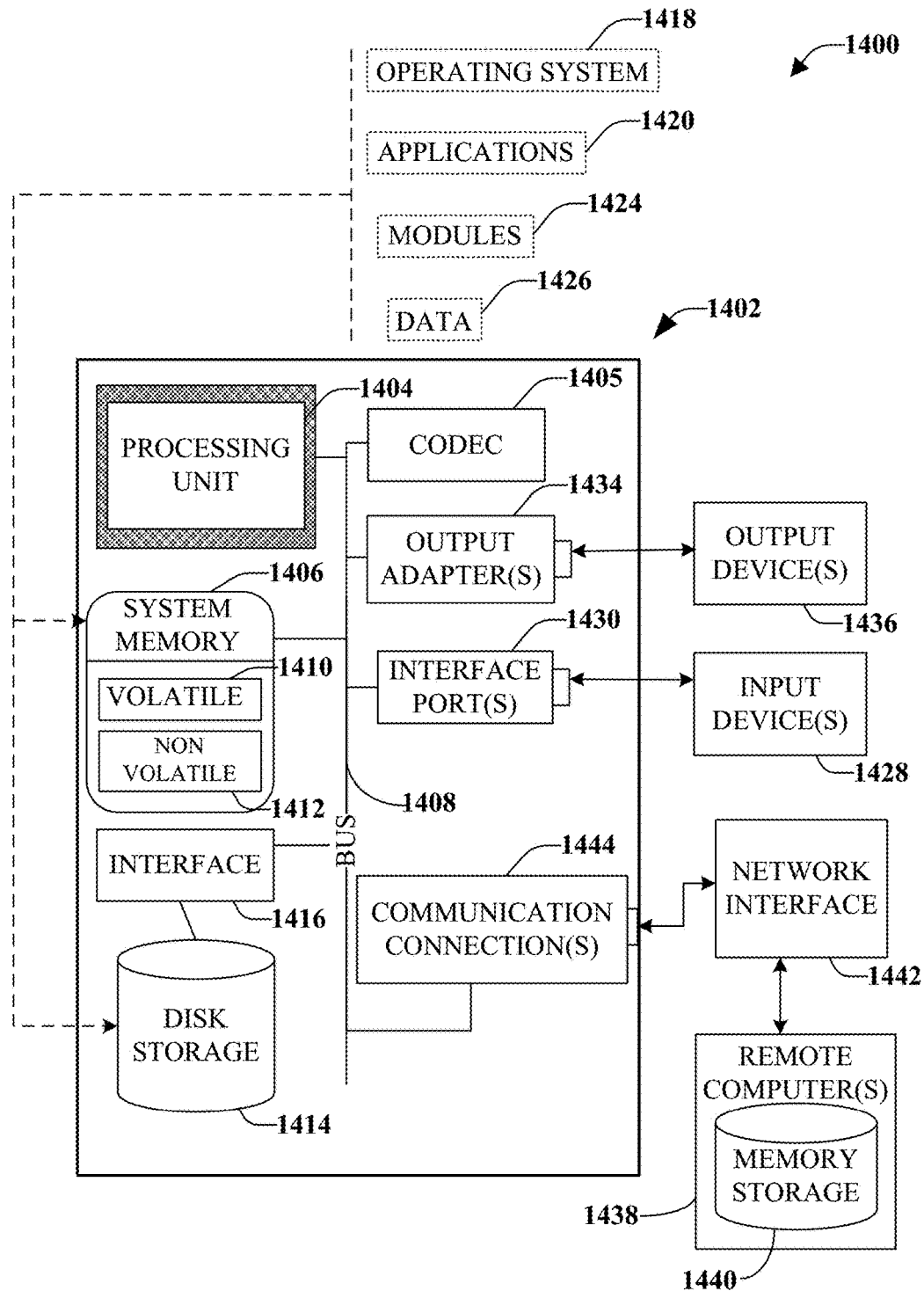
FIG. 14 is a schematic block diagram illustrating a suitable operating environment in accordance with various aspects and embodiments.

With reference to FIG. 14, a suitable environment 1400 for implementing various aspects of the claimed subject matter includes a computer 1402. The computer 1402 includes a processing unit 1404, a system memory 1406, a codec 1405, and a system bus 1408. The system bus 1408 couples system components including, but not limited to, the system memory 1406 to the processing unit 1404. The processing unit 1404 can be any of various available processors. Dual microprocessors and other multiprocessor architectures also can be employed as the processing unit 1404.

The system bus 1408 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1494), and Small Computer Systems Interface (SCSI).

The system memory 1406 includes volatile memory 1410 and non-volatile memory 1412. The basic input/output system (BIOS), containing the basic routines to transfer information between elements within the computer 1402, such as during start-up, is stored in non-volatile memory 1412. In addition, according to present innovations, codec 1405 may include at least one of an encoder or decoder, wherein the at least one of an encoder or decoder may consist of hardware, a combination of hardware and software, or software. Although, codec 1405 is depicted as a separate component, codec 1405 may be contained within non-volatile memory 1412. By way of illustration, and not limitation, non-volatile memory 1412 can include read only memory (ROM), programmable ROM (PROM), electrically programmable ROM (EPROM), electrically erasable programmable ROM (EEPROM), or flash memory. Volatile memory 1410 includes random access memory (RAM), which acts as external cache memory. According to present aspects, the volatile memory may store the write operation retry logic (not shown in FIG. 14) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM.

Computer 1402 may also include removable/non-removable, volatile/non-volatile computer storage medium. FIG. 14 illustrates, for example, disk storage 1414. Disk storage 1414 includes, but is not limited to, devices like a magnetic disk drive, solid state disk (SSD) floppy disk drive, tape drive, Jaz drive, Zip drive, LS-70 drive, flash memory card, or memory stick. In addition, disk storage 1414 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1414 to the system bus 1408, a removable or non-removable interface is typically used, such as interface 1416.

It is to be appreciated that FIG. 14 describes software that acts as an intermediary between users and the basic computer resources described in the suitable operating environment 1400. Such software includes an operating system 1418. Operating system 1418, which can be stored on disk storage 1414, acts to control and allocate resources of the computer system 1402. Applications 1420 take advantage of the management of resources by operating system 1418 through program modules 1424, and program data 1426, such as the boot/shutdown transaction table and the like, stored either in system memory 1406 or on disk storage 1414. It is to be appreciated that the claimed subject matter can be implemented with various operating systems or combinations of operating systems.

A user enters commands or information into the computer 1402 through input device(s) 1428. Input devices 1428 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1404 through the system bus 1408 via interface port(s) 1430. Interface port(s) 1430 include, for example, a serial port, a parallel port, a game port, and a universal serial bus (USB). Output device(s) 1436 use some of the same type of ports as input device(s). Thus, for example, a USB port may be used to provide input to computer 1402, and to output information from computer 1402 to an output device 1436. Output adapter 1434 is provided to illustrate that there are some output devices 1436 like monitors, speakers, and printers, among other output devices 1436, which require special adapters. The output adapters 1434 include, by way of illustration and not limitation, video and sound cards that provide a means of connection between the output device 1436 and the system bus 1408. It should be noted that other devices and/or systems of devices provide both input and output capabilities such as remote computer(s) 1438.

Computer 1402 can operate in a networked environment using logical connections to one or more remote computers, such as remote computer(s) 1438. The remote computer(s) 1438 can be a personal computer, a server, a router, a network PC, a workstation, a microprocessor based appliance, a peer device, a smart phone, a tablet, or other network node, and typically includes many of the elements described relative to computer 1402. For purposes of brevity, only a memory storage device 1440 is illustrated with remote computer(s) 1438. Remote computer(s) 1438 is logically connected to computer 1402 through a network interface 1442 and then connected via communication connection(s) 1444. Network interface 1442 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1444 refers to the hardware/software employed to connect the network interface 1442 to the bus 1408. While communication connection 1444 is shown for illustrative clarity inside computer 1402, it can also be external to computer 1402. The hardware/software necessary for connection to the network interface 1442 includes, for exemplary purposes only, internal and external technologies such as, modems including regular telephone grade modems, cable modems and DSL modems, ISDN adapters, and wired and wireless Ethernet cards, hubs, and routers.

Referring now to FIG. 15, there is illustrated a schematic block diagram of a computing environment 1500 in accordance with this disclosure. The system 1500 includes one or more client(s) 1502 (e.g., laptops, smart phones, PDAs, media players, computers, portable electronic devices, tablets, and the like). The client(s) 1502 can be hardware and/or software (e.g., threads, processes, computing devices). The system 1500 also includes one or more server(s) 1504. The server(s) 1504 can also be hardware or hardware in combination with software (e.g., threads, processes, computing devices). The servers 1504 can house threads to perform transformations by employing aspects of this disclosure, for example. One possible communication between a client 1502 and a server 1504 can be in the form of a data packet transmitted between two or more computer processes wherein the data packet may include video data. The data packet can include a metadata, e.g., associated contextual information, for example. The system 1500 includes a communication framework 1506 (e.g., a global communication network such as the Internet, or mobile network(s)) that can be employed to facilitate communications between the client(s) 1502 and the server(s) 1504.

Communications can be facilitated via a wired (including optical fiber) and/or wireless technology. The client(s) 1502 include or are operatively connected to one or more client data store(s) 1508 that can be employed to store information local to the client(s) 1502 (e.g., associated contextual information). Similarly, the server(s) 1504 are operatively include or are operatively connected to one or more server data store(s) 1510 that can be employed to store information local to the servers 1504.

In one embodiment, a client 1502 can transfer an encoded file, in accordance with the disclosed subject matter, to server 1504. Server 1504 can store the file, decode the file, or transmit the file to another client 1502. It is to be appreciated, that a client 1502 can also transfer uncompressed file to a server 1504 and server 1504 can compress the file in accordance with the disclosed subject matter. Likewise, server 1504 can encode video information and transmit the information via communication framework 1506 to one or more clients 1502.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

What is claimed is:

1. A system, comprising:
a processor configured to execute computer executable components stored in a memory:
an interface component configured to generate an interface that facilitates tracking course of care of a patient, wherein the interface comprises a plurality of input compartments defined by a first axis comprising columns corresponding to sequential points in time over the course of the care and a second axis comprising rows respectively corresponding to patient care events or patient conditions associated with the course of the care;
a reception component configured to receive input regarding a patient care event or patient condition that occurred over the course of care;
a logging component configured to fill one or more input compartments respectively corresponding to a point or period of time associated with occurrence of the patient care event or patient condition;
a tracking component configured to employ at least one algorithm and at least one information source that defines relationships between patient conditions, patient care events, and a course of patient care to infer issues associated with a condition of the patient;
an inference component configured to:
infer when the interface component should add one or more additional patient care events or patient conditions to the interface based on relationships between patient care events and/or patient care conditions, a course of patient care, and a current point in the course of the patient care, wherein the inference is probabilistic;
identify a specific context or action based on the inference; and
construct one or more new events or actions; and
a patient tracking tool configured to add one or more data fields based on the one or more new events or actions.

2. The system of claim 1, further comprising a presentation component configured to display the interface.

3. The system of claim 1, wherein the reception component is configured to receive the input in real time over the course of care.

4. The system of claim 1, further comprising a time component configured to track progression of time over the course of care, wherein the logging component is configured to determine the point or period of time associated with the occurrence of the patient care event or patient condition based in part on a time of receipt of the input.

5. The system of claim 1, further comprising a time component configured to track progression of time over the course of care, wherein the input regarding the patient care event or patient condition identifies a time of onset of the patient care event or patient condition, and wherein the logging component is configured to automatically fill input compartments of a row corresponding to the patient care event or patient condition over the course of care until new input is received that identifies a change in the patient care event or patient condition.

6. The system of claim 1, wherein the input relates to at least one of: a time of onset of the patient care event or patient condition, a duration of time elapsed since onset of the patient care event or patient condition, or a time of change in the patient care event or patient condition.

7. The system of claim 1, wherein the input relates to a characteristic of the patient care event or patient condition.

8. The system of claim 1, wherein the logging component is configured to fill the one or more input compartments with data that represents at least one of the occurrence of the patient care event or patient condition, or a characteristic of the patient care event or patient condition, and wherein the data comprises at least one of a color, a pattern, a symbol or text.

9. The system of claim 1, wherein at least one of the input compartments includes a drop down menu with input options that facilitate selection of one of the options for the input.

10. The system of claim 1, wherein the reception component is configured to receive the input from a user via an input device.

11. The system of claim 1, wherein the reception component is configured to receive the input from a medical device.

12. The system of claim 1, wherein the patient care events or patient conditions respectively associated with the rows are predefined.

13. The system of claim 1, wherein the interface component is configured to receive user input defining a patient care event or patient condition associated with one or more of the rows.

14. The system of claim 1, further comprising a time component configured to track progression of time over the course of care, wherein the interface component is configured to add additional columns corresponding to current points in time as the course of care continues.

15. The system of claim 1, further comprising a time component configured to track progression of time over the course of care, wherein the interface component is configured to add one or more additional rows corresponding to a new patient event or new patient condition relevant to the course of care as the course of care continues.

16. The system of claim 1, wherein the inference component is configured to employ one or more classifiers to:
determine a confidence that certain input belongs to a certain class; and
infer an action that a user desires to be automatically performed based on the classification.

17. A method comprising:
using a processor to execute the following computer executable instructions stored in a memory to perform the following acts:
generating an interface that facilitates tracking course of care of a patient, wherein the interface comprises a plurality of input compartments defined by a first axis comprising columns corresponding to sequential points in time over the course of the care and a second axis comprising rows respectively corresponding to patient care events or patient conditions associated with the course of the care;
receiving input regarding a patient care event or patient condition that occurred over the course of the care;
filling one or more input compartments respectively corresponding to a point or period of time associated with occurrence of the patient care event or patient condition, in response to reception of the input;
employing at least one algorithm and at least one information source that defines relationships between patient conditions, patient care events, and a course of patient care to infer issues associated with a condition of the patient;
inferring when the interface should display one or more additional patient care events or patient conditions within the interface based on relationships between patient care events and/or patient care conditions, a course of patient care, and a current point in the course of the patient care, wherein the inference is probabilistic;
identifying a specific context or action based on the inference;
constructing one or more new events or actions; and
adding one or more data fields based on the one or more new events and actions.

18. The method of claim 17, further comprising displaying the interface at a device.

19. The method of claim 17, further comprising:
tracking progression of time over the course of care; and
determining the point or period of time associated with the occurrence of the patient care event or patient condition based in part on a time of receipt of the input.

20. The method of claim 17, further comprising:
tracking progression of time over the course of care, wherein the input regarding the patient care event or patient condition identifies a time of onset of the patient care event or patient condition; and
automatically filling input compartments of a row corresponding to the patient care event or patient condition over the course of care until new input is received that identifies a change in the patient care event or patient condition.

21. A non-transitory computer-readable medium comprising computer-readable instructions that, in response to execution, cause a computing system to perform operations, comprising:
generating an interface that facilitates tracking a course of care of a patient, wherein the interface comprises a plurality of input compartments defined by a first axis comprising columns corresponding to sequential points in time over the course of the care and a second axis comprising rows respectively corresponding to patient care events or patient conditions associated with the course of the care;
filling one or more input compartments respectively corresponding to a point or period of time associated with occurrence of a patient care event or a patient condition based on input regarding the occurrence of the patient care event or the patient condition;
displaying the interface via a display screen of a device;
employing at least one algorithm and at least one information source that defines relationships between patient conditions, patient care events, and a course of patient care to infer issues associated with a condition of the patient;
inferring when the interface should display one or more additional patient care events or patient conditions within the interface based on relationships between patient care events and/or patient care conditions, a course of patient care, and a current point in the course of the patient care, wherein the inference is probabilistic;
identifying a specific context or action based on the inference;
constructing one or more new events or actions; and
adding one of more new data fields based on the one or more new events or actions.

* * * * *